United States Patent [19]

Uchida et al.

[11] Patent Number: 4,820,529

[45] Date of Patent: Apr. 11, 1989

[54] PROCESS FOR PREPARING PASTY PROTEINOUS MATERIAL OR PROTEINOUS FOOD FROM CRUSTACEANS

[75] Inventors: Yasuzo Uchida; Hitoshi Nagasaki; Makoto Itoh, all of Tokyo, Japan

[73] Assignee: Asahi Denka Kogyo Kabushiki Kaisha, Tokyo, Japan

[21] Appl. No.: 65,264

[22] Filed: Jun. 22, 1987

[30] Foreign Application Priority Data

Jun. 26, 1986 [JP] Japan .................................. 61-149994
May 8, 1987 [JP] Japan .................................. 62-113306

[51] Int. Cl.$^4$ ......................... A23J 1/04; A23L 1/325
[52] U.S. Cl. ..................................... 426/7; 426/643; 426/657
[58] Field of Search ................ 426/7, 56, 59, 643, 426/656, 657

[56] References Cited

U.S. PATENT DOCUMENTS 3,249,442 5/1966 Keyes et al. .
3,256,098 6/1966 Ohtaki et al. ........................ 426/7
4,036,993 7/1977 Ikeda et al. .
4,294,856 10/1981 Kinumaki et al. .

FOREIGN PATENT DOCUMENTS 0479521 6/1975 Australia ................................ 426/7
0096902 12/1983 European Pat. Off. .
2308320 11/1976 France .
63140 4/1984 Japan .

OTHER PUBLICATIONS

Chemical Abstracts vol. 88, No. 17, Apr. 1978, (Columbus, Ohio, U.S.), see pg. 416, abstract 119596f, & JP, A, 77128259 (Nippon Suisan Kaisha, Ltd.) Oct. 27, 1977.
Chem. Abstract 93: 148442m.

*Primary Examiner*—Marianne Cintins
*Attorney, Agent, or Firm*—Frishauf, Holtz, Goodman & Woodward

[57] ABSTRACT

According to the process of the present invention for preparing a pasty proteinous material or a proteinous food, crustaceans are boiled and milled under sufficient conditions for inactivating enzymes contained therein and then proteolytic enzyme(s) and/or microorganism(s) are allowed to act thereon. Thus various protein sources including crustacean meat remaining in the trunks and carapaces, which have been disposed hitherto, can be efficiently utilized.

10 Claims, No Drawings

PROCESS FOR PREPARING PASTY PROTEINOUS MATERIAL OR PROTEINOUS FOOD FROM CRUSTACEANS

BACKGROUND OF THE INVENTION

1. Field of the Invention:

This invention relates to a process for preparing a pasty proteinous material or a proteinous food.

2. Description of the Prior Art:

Regarding the utilization of crustaceans such as crabs, limbs and claws thereof have been efficiently used and formulated into limb- or stick-like meat products or claw meat products. After removing the carapaces, gonads, branchiae and internals, the trunks are washed with water and ground. Then the meat remaining in the trunks is recovered with a meat separator and formulated into minced meat. This meat is further washed with water and fibrous meat taken therefrom is formulated into flakes. Thus various proteineous parts including meat remaining in the carapace, the glands, which are mostly unutilized although taken as "kanimiso" in the case of some crabs, branchiae and meat remaining in the trunks are not utilized but disposed as such.

As described above, most of crabs are marketed in the form of headless shelled products by removing the heads, limbs and other organs thereof and proteinous parts including residual head meat and residual limb meat are not utilized but disposed at present. From the viewpoint of the efficient utilization of these valuable food resources, there has been required to develop a proteinous material or a proteinous food by efficiently utilizing the residual meat of crustaceans.

Reports of the Shizuoka Prefectural Research Institute No. 24,125 (1980) has disclosed a process for preparing a paste from fish heads. Further Japanese Patent Laid-Open No. 63140/1984, No. 63141/1984, No. 63142/1984, No. 63143/1984 and No. 63144/1984 have disclosed each a process for preparing a pasty proteinous material by enzymatically treating fish meat. However crustaceans treated by these methods would turn black, which makes it difficult to apply these products as foods.

In addition, crustaceans ground together with carapaces and frozen would liberate water on thawing, be rough to the palate and have a poor flavor, which makes these products hardly available as foods.

SUMMARY OF THE INVENTION

It is an object of the present invention to provide a process for preparing a proteinous material or a proteinous food by efficiently utilizing residual meat and carapaces of crustaceans which have been disposed hitherto.

It is another object of the present invention to provide a process for preparing a pasty proteinous material or a proteineous food which undergoes no discoloration; is smooth and palatable; has an excellent texture; shows no liberation of water on thawing; is highly compatible with other food materials; and has the characteristics inherent in crustaceans, e.g., crabs or shrimps.

We have attempted to efficiently utilize unused protein sources such as crab trunks or shrimp heads and simultaneously utilize calcium, iron and chitin (chitosan) which exerts an effect of lowering blood cholesterol, contained in the carapaces of crabs and shrimps in the field of food. As a result, we have found that a pasty proteinous material or a proteinous food which undergoes no discoloration; is smooth and palatable; has an excellent texture; shows no liberation of water on thawing; is highly compatible with other food materials; and has the characteristics inherent in crustaceans, e.g., crabs or shrimps; can be obtained by thermally inactivating discoloring enzymes or autolytic enzymes contained in crab trunks, crab heads and/or crabs and shrimps, which have not been efficiently utilized hitherto, and then milling the carapaces containing calcium, iron and chitosan which are effective on man; thermally inactivating the abovementioned enzymes after milling the above materials; or simultaneously carrying out these two procedures together; and then exposing the obtained product to proteolytic enzyme(s) and/or microorganism(s), thus completing the present invention.

Accordingly, the present invention provides a process for preparing a pasty proteinous material or a proteinous food from crustaceans which comprises the steps of:

boiling and milling crustaceans under such conditions so to sufficiently inactivate enzymes contained therein; and exposing the boiled and milled crustaceans as obtained above, which are in the form of a slurry, to proteolytic enzyme(s) and/or microorganism(s).

DETAILED DESCRIPTION OF THE INVENTION

Examples of the crustaceans to be used in the present invention are those which are conventionally employed in processing fishery products, such as crabs, e.g., king crab, *latrpillia phalangium*, ternner crab, red turnner crab, *paralithodes breripes, maja spirigera*, mask crab, *leucosia obtasifrons*, hairy crab and blue crab and shrimps, e.g., tiger prawn, *Metapenaeus joyneri*, krill, *Palaemon nipponensis*, shrimp, lobster, crawfish and *Upogekia major*.

Examples of the proteolytic enzymes are proteinases such as acrosin, urokinase, uropepsin, elastase, enteropeptidase, cathepsin, kallikrein, kininase 2, chymotrypsin, chymopapain, collagenase, streptokinase, subtilisin, thermolysin, trypsin, thrombin, papain, pancreatin peptidase, ficin, plasmin, renin peptidase and rennin; aminopepetidases such as arginine aminopeptidase, oxynase and leucin aminopeptidase; angiotensinase, angiotensin converting enzyme and insulinase; carboxypeptidases such as arginine carboxypeptidase, kininase 1 and thyroid peptidase; dipeptidases such as carnosinase and prolinase; peptidases such as pronase; and other proteolytic enzymes as well as denatured products and compositions thereof.

Examples of the proteolytic microorganisms to be used in the present invention are molds belonging to the genera Aspergillus, Mucor, Rhizopus, Penicillium and Monascus; lactic acid bacteria belonging to the genera Streptococcus, Pediococcus, Leuconostoc and Lactobacillus; bacteria such as *Bacillus natto* and *Bacillus subtilis;* and yeasts such as *Saccharomyces ellipsuideus, Saccharomyces cerevisiae* and Torulla; as well as mutants and compositions thereof.

A preferable example of the process of the present invention may be carried out as follows.

First, the abovementioned discoloring enzymes and/or useless enzymes contained in the trunks or whole bodies of crabs or shrimps are inactivated by (1) boiling the material at a temperature higher than the inactivation temperatures of these enzymes: or (2) adding chemical(s) such as hydrogen peroxide capable of inactivating the same and then boiling the mixture at a temperature lower than the inactivation temperatures as described in (1) and lower than the gelation temperatures of the proteins contained therein.

Subsequently the carapaces of the crabs or shrimps are milled to such an extent as to give no feeling of roughness to the human palate. This milling may be carried out either before the above boiling treatment or simultaneously therewith. The milling may be effected with the use of a mill such as a stone mill. It is particularly advantageous to repeat this treatment several times to thereby give bone and carapace particles of $200\mu$ or below, preferably $150\mu$ or below, in diameter.

The relationship between the extent of milling and texture is evaluated by ten panelists. As a result, all panelists evaluate particles of $300\mu$ or above in diameter as rought and those of 200 to $300\mu$ therein as somewhat rough. On the other hand, two panelists and none evaluate those of 150 to $200\mu$ and $150\mu$ or below as rough, respectively.

Then the thermally treated, i.e., boiled and milled crustacean meat, which is in the form of a slurry, is homogeneously mixed with the proteolytic enzyme(s) and/or microorganism(s) as described above by (1) adding the above enzyme(s) and/or microorganism(s) to the heated and milled crustacean meat and further milling the crustacean meat by applying various mechanical forces thereto; or (2) further milling the heated and milled crustacean meat by applying various mechanical forces thereto while adding the above enzyme(s) and/or microorganism(s) thereto and further applying mechanical force(s) thereto, if required, to thereby further mill the mixture followed by homogeneously mixing these materials.

Then various additives such as animal protein source(s), vegetable protein source(s) and animal or vegetable fat and oil source(s) other than the crab or shrimp meat, carbohydrate source(s), inorganic salt(s) such as common salt, disodium phosphate or sodium polyphosphate, perfume(s), seasoning(s), corrigen(s), antibacterial agent(s), water, fat(s) and oil(s), enzyme(s) and/or microorganism(s) acting on, for example, carbohydrates, emulsifier(s), colorant(s), vitamin(s), preservative(s), sweetener(s), amino acid(s), highly unsaturated fatty acid(s), vegetable extract(s) and tasting agent(s) may be introduced into the above mixture, without departing from the scope of the present invention. These additives may be added to the paste of the crab or shrimp meat after treating the same with the proteolytic enzyme(s) and/or mixroorganism(s). However it is highly desirable to homogeneously add these additives or sources thereof to the crustacean material before or, at least, during the treatment with the proteolytic enzyme(s) and/or microorganism(s) in order to give a homogeneous product. Thus a highly stable system wherein these additives or sources thereof are homogeneously dissolved, emulsified and/or dispersed can be formed. However it is preferable to add edible animal and vegetable fats and oils thereto after the completion of the treatment with the above enzyme(s) and/or microorganism(s), since these materials would sometimes lower the effects of the enzyme(s) or microorganism(s).

Furthermore other additives such as fat(s), oil(s), enzyme(s) or microorganism(s) acting on carbohydrates and water may be added thereto.

One of the features of the present invention resides in the thermal treatment of the trunks, heads or whole bodies of crabs or shrimps. This treatment may be effected by boiling crabs or shrimps in a tank in a conventional manner; by milling the trunks, heads or whole bodies of crabs or shrimps, which are optionally frozen previously, to give a slurry and then heating the slurry in a pot under stirring; by adding, for example, hydrogen peroxide to the above slurry and heating the resulting mixture under stirring; by continuously heating the materials with the use of a continuous heater; or by continuously heating the above slurry to which additive(s) such as hydrogen peroxide are added.

The heating temperature may be within the range of 30° to 140° C., preferably 70° to 120° C. When hydrogen peroxide is to be used, the heating may be preferably carried out at 30° to 60° C.

This thermal treatment may be carried out for several seconds to one hour, depending on the temperature.

Examples of the abovementioned vegetable protein sources to be used as additives are vegetable proteins such as soybean, peanut, cotton seed, sesame, sunflower and wheat, defatted products thereof and protein concentrates and separated proteins derived therefrom.

Examples of the abovementioned animal protein sources to be used as additives are milk or dairy products such as livestock milk, defatted milk, condensed milk, whole milk powder, modified milk powder, butter, cream and cheese; livestock or poultry meats such as beef, horsemeat, pork, mutton, chicken, duck flesh, goose flesh and turkey; processed meat products such as smoked or dried meats; eggs or processed eggs such as eggs, dried eggs, frozen eggs, yolk and albumen; processed fish meats such as minced meats and ground meats; and other animal protein sources such as liver.

Examples of the abovementioned animal or vegetable fat and oil sources are animal fats and oils such as lard, beef tallow, mutton tallow, horse tallow, fish oil, whale oil and milk fat; vegetable fats and oils such as soybean oil, linseed oil, safflower oil, sunflower oil, cotton seed oil, kapok oil, olive oil, wheat germ oil, corn oil, palm oil, palm kernel oil, sal fat, illipe fat, Borneo taro fat and coconut oil; processed fats and oils obtained by hydrogenating, transesterifying or fractionating them; and fat and oil products such as butter, cream, margarine and shortening.

Examples of the abovementioned carbohydrate sources are agricultural products containing a large amount of carbohydrates such as rice, wheat, corn, potato and sweet potato; powdery products obtained therefrom; starch products obtained therefrom; such as rice starch, wheat starch, corn starch and potato starch; processed or denatured starch products such as α-starch and dextrin; sugars such as sugar, honey and starch sugar; and fresh flesh or fruit juice of apple, orange, strawberry and grape.

Examples of the vitamins to be added to the proteineous material of the present invention are vitamin A, vitamin $B_1$, vitamin $B_2$, vitamin $B_{12}$, vitamin C, vitamin D, pantothenic acid, vitamin E, vitamin H, vitamin K, vitamin L, bitamin M, nicotinic acid, vitamin P, thioctic acid, thioctamide, vitamin R, vitamin S, vitamin T, vitamin U, vitamin V, vitamin W, vitamin X, vitamin Y, rutin and orotic acid. Examples of the abovementioned amino acids are L-glutamic acid (salt), L-glutamine, glutathione, glycyclglycine, D,L-alanine, L-alanine, γ-aminobutyric acid, L-arginine (hydrochloride), L-aspartic acid (salt), L-asparagine, L-citrulline, L-tryptophan, L-threonine, glycine, L-cysteine (derivative), L-histidine (salt), L-hydroxyproline, L-isoleucine, L-leucine, L-lysine (salt), D,L-methionine, L-methionine, L-ornithine (salt), L-phenylalanine, D-phenylglycine, L-proline, L-serine, L-tyrosine and L-valine. Examples of the highly unsaturated fatty acids are linoleic acid, linolenic acid, eicosapentaenoic acid and docosahexaenoic acid as well as glycerides thereof. Examples of the vegetable extracts are extracts of various plants such as medicinal herbs, asparagus and ginseng.

When added to the slurry of crab or shrimp meat optionally mixed with the abovementioned additives, the proteolytic enzyme(s) and/or microorganism(s) as described above would begin to act on the slurry optionally mixed with the additives. Thus it is required to maintain the mixture thus obtained at an appropriate temperature for an appropriate period. The temperature and period such as those described above may be determined depending on various factors such as the enzyme(s) and/or microorganism(s) to be used, the flavor of the aimed pasty proteinous material and the extent of the decomposition of the crab or shrimp meat. Generally speaking, a temperature of 0° to 80° C. and a period of 0.5 minute to 30 days are required. The mixture may be maintained at a constant temperature throughout the period. Alternately, it may be maintained at a certain temperature for a while and then at a different temperature, i.e., multi-step controlling. After adding the abovementioned enzyme(s) and/or microorganism(s) to the slurry of crab or shrimp meat, the resulting mixture is homogenized by applying mechanical force(s) thereto or by mixing them under stirring, as described above. The mixture may be maintained at the above temperature for the above period while applying the mechanical force(s) thereto. Alternately, the application of the mechanical force(s) thereto may be ceased when a homogeneous mixture is obtained and then aging may be effected. In this case, the mixture may be maintained at the above temperature during the application of the mechanical force(s) as well as the following aging period.

The temperature at which the mixture is to be maintained may be broadly classified into a low temperature range (0° to 15° C.), a moderate temperature range (15° to 35° C.) and a high temperature range (35° to 80° C.). When enzyme(s) are to be used alone, the mixture may be maintained at a temperature within the high or moderate temperature range in the first step and then at a temperature within the low temperature range in the second step. When enzyme(s) are used together with microorganism(s), the mixture is treated with the enzyme(s) at a temperature within the high, moderate or low temperature range in the first step followed by optional inactivation of the enzyme(s) by cooling, if required. Then the microorganism(s) are added to give a homogeneous mixture, which is then maintained at a temperature within the moderate or low temperature range. When microorganism(s) are to be added alone, it is desirable to maintain the mixture at a temperature within the low or moderate temperature range.

It is preferable that the pasty proteinous material or proteinous food as prepared by the process of the present invention is treated with the enzyme(s) and/or microorganism(s) to give the content of water-soluble proteins, which mean a protein fraction which is not precipitated even by adding a solution of sodium trichloroacetate, of 5 to 50%, preferably 30 to 45% (5 to 40%, preferably 20 to 35%, when animal and/or vegetable protein source(s) are further employed) based on the total proteins. When the content of the water-soluble proteins is less than 5%, muscle fibers of the crab or shrimp meat remaining in the product give an unsatisfactory smoothness. On the other hand, when the content thereof exceeds 50% or 40% (when animal and/or vegetable protein source(s) are further employed), the obtained product would exhibit an undesirable bitter taste. It is particularly preferable that the proteinous material of the present invention contains 40 to 90% by weight of peptides of molecular weight of 40,000 to 70,000 based on the total peptides except water-soluble peptides and amino acids.

When allowed to stand, proteins in the pasty proteinous material thus obtained would further decompose with the elapse of time, which alters the aimed physicochemical properties and flavor of the product. Thus it should be immediately employed in the preparation of a solid, flowable or liquid food wherein the enzyme(s) and/or microorganism(s) contained in the pasty proteinous material are inactivated by thermal treatment(s) included in the preparation process. Alternately when the above material is not immediately employed in the preparation of a solid, flowable or liquid food, it should be stored after the thermal treatment to thereby inactivate the enzyme(s) and/or microorganism(s); freezing or drying by, for example, spraying without inactivating the enzyme(s) and/or microorganism(s); or adding some substance(s) capable of inactivating the enzyme(s) and/or microorganism(s) thereto.

The aimed product, i.e., a pasty proteinous material or a proteinous food, prepared by the process of the present invention, which is obtained from some portions or whole bodies of crabs or shrimps and contains a large amount of proteins, may be used as such in, for example, oden (Japanese hotchpotch), gruel, noodles, terrine, mousse, meat balls, filling of harumaki (Chinese fried rolled meat), coating of gyoza or wantan (Chinese stuffed dumpling), filling of shaomai, weaning foods, custard pudding-like food, tofulike food, yoghurt-like food, thickening or filling for hamberger steak, flake-type food, proteinous drink, soups, spreads, flowable foods for stick or aged persons, sauce, pot-steamed type food, cheese-like food, noodle-like food, mayonnaise-like food, terrine-like food, noodle-like food, mayonnaise-like food, terrine-like food, fried foods and coatings for various foods. It may be further used as a starting material for the preparation of these foods, which makes it highly useful.

Furthermore, the aimed product prepared by the process of the present invention may be mixed with, for example, animal protein source(s), vegetable protein source(s), animal and/or vegetable fat(s) and oil(s) and carbohydrate(s) and the resulting mixture may be used as a food as such or as a food material.

With the use of the aimed product prepared by the process of the present invention, various foods may be prepared by, for example, the following methods.

(1) The aimed product obtained by the process of the present invention is mixed with, for example, animal and/or vegetable fat(s) or oil(s) such as a vegetable oil or butter, flux(es) such as phosphates, for example, secondary sodium phosphate, sodium polyphosphate or sodium pyrophosphate and, if required, other animal protein source(s) such as cheese or casein sodium, seasoning(s), food preservative(s), carbohydrate(s) such as crab, shrimp, beef, pork, chicken, liver or short-necked clam pieces, flavor(s) and extract(s). The mixture thus obtained is molten by heating to 50° to 100° C. under stirring to give a homogeneous mixture. After cooling, a process cheese-like, cheese-spread-like or liver paste-like solid or spread food is obtained.

(2) To the aimed product prepared by the process of the present invention, water is added and the resulting mixture is ground, if required, to give a slurry. Further gelling agent(s) such as agar, furcellaran, carrageenan, pectin, gelatin, yolk, whole egg or albumen; inhibitor(s) against water liberation such as starch; and other additives such as sweetener(s), seasoning(s), perfume(s) and colorant(s) are added to the slurry, if required. After homogeneously mixing and heating, the mixture is cooled to give an elastic gelatinous food similar to, for example, custard pudding or jelly.

(3) To the aimed product prepared by the process of the present invention, water is added followed by, if requried, carrageenan, agar, defatted milk or other dairy products and fermentation accelerator(s) such as glucose or lactose. Then the resulting mixture is ground to thereby give a slurry containing 2 to 10% of proteins. This slurry is thermally pasteurized and lactic acid bacteria are added thereto to effect fermentation. Various additives such as sweetener(s), perume(s), seasoning(s) or colorant(s) may be further added thereto, if required, at any step of the above procedure. Thus a flowable or liquid food product similar to, for example, yoghurt or lactic acid drinks is obtained.

(4) The aimed product prepared by the process of the present invention is mixed with an aqueous medium in which various components are dissolved, such as water, soybean milk, milk, fruit juice or vegetable juice while, if required, milling. Thus nitrogen-containing components of the above product soluble in water are dissolved in the medium while those insoluble in water are homogeneously dispersed therein. Then the resulting system is thermally pasteurized. Alternately an aqueous medium is added at any step in the preparation of the aimed product according to the present invention and the resulting mixture is adjusted to an appropriate concentration and treated with enzyme(s) and/or microorganism(s). Thus a drink is prepared.

(5) The aimed product prepared by the process of the present invention in an amount of 0.1 to 15 parts by weight on a solid base is mixed with 100 parts by weight of wheat flour. Then appropriate additives depending on the aimed wheat flour product are added to the mixture to give a dough. This dough is appropriately treated by, for example, baking, steaming or frying to give a wheat flour product such as biscuit, cookie, wafer, cracker, pretzel, cake, pie, coating of cream puff, doughnut, hot cake, bread, pizza pie, okonomiyaki, takoyaki, coating of bun stuffed with minced meat, coating of bun stuffed with bean jam, coating of shaomai, coating of harumaki or coating of gyoza.

(6) The aimed product prepared by the process of the present invention in an amount of 0.1 to 40 parts by weight on a solid basis is mixed with 100 parts by weight of soybean protein. Further various additives such as seasoning(s), spice(s) or colorant(s), animal or vegetable fat(s) or oil(s), animal protein source(s), vegetable protein source(s), carbohydrate source(s), luxuries, vegetables, meat(s) and/or fish(es) may be added to the mixture, if required. Then the soybean protein is solidified to give a soybean protein processed food such as tofu, aburaage, ganmodoki, namaage, yuba, koridofu, fibrous soybean protein food, soybean protein curd, structured soybean protein food or soybean protein gelatinous food.

(7) The aimed product prepared by the process of the present invention in an amount of 0.1 to 15% (by weight; the same will apply hereinafter) is added to an aqueous medium such as water or an aqueous solution in which other component(s) are dissolved and the mixture is milled, if required. Then 10 to 90% of an edible animal or vegetable fat or oil is added thereto and the obtained mixture is emulsified with the use of, if required, emulsifier(s) and/or emulsification stabilizer(s) for giving a more stable emulsion. Thus an emulsified fat or oil composition which forms an oil-in-water type emulsion and is to be introduced into a dough or treating the surface of the same available in the preparation of, for example, noodles, bread, rice cracker, pie, biscuit, cracker, coating of gyoza, cakes or coating of cream puff;a spread for breads; or a topping or filling of various foods can be obtained.

(8) The aimed product prepared by the process of the present invention, which is further heated and milled, if required, in an amount of 0.1 to 10 parts by weight, preferably 0.1 to 5 parts by weight, on a solid basis is steamed together with 100 parts by weight of rice or rice mill; or separately heated and then pounded together with the steamed rice or rice mill to thereby give a rice cake dough, which is then molded and toasted or fried, if required, to give a rice cracker.

In the above process, the enzyme(s) and/or microorganism(s) may be inactivated either during the preparation of the pastry product or by the thermal treatment in the preparation of the rice cracker.

(9) The aimed product prepared by the process of the present invention in an amount of 0.1 to 10 parts by weight, preferably 0.1 to 5 parts by weight, on a solid basis, is used per 100 parts by weight of wheat flour. The above product is dissolved in, for example, water prior to mixing of the wheat flour with other components such as water, eggs or milk. Alternately, the above product is added when the wheat flour is mixed with the other components or thereafter, depending on the type of the aimed noodle product. Thus products which mainly comprise wheat flour and are cooked before eating, i.e., noodles in a wide sense, such as so-called noodles including udon, soba or Chinese noodles as well as nouille, gnocchis, spaghetti and macaroni can be obtained.

In the above process, the enzyme(s) and/or microorganism(s) may be inactivated either during the preparation of the product of the present invention or by the final thermal treatment.

(10) The aimed product prepared by the process of the present invention is used in an amount of 0.1 to 20 parts by weight, preferably 0.1 to 10 parts by weight, on a solid basis. Other appropriate components are added thereto to give a batter for fried foods such as fishes, livestock meats, poultry meats, algae, vegetables and mushrooms can be obtained. These foods coated with the above batter may be optionally further crumbed. These fried foods include not only those to be taken immediately after frying but also those to be taken after refrigerating, i.e., so-called chilled foods, and/or those to be taken after freezing, i.e., so-called precooked frozen foods.

(11) The aimed product prepared by the process of the present invention is added at any step in the preparation of a paste, solid, powdery, liquid or flowable seasoning such as sauce, soysauce, miso, stock, curry sauce, broth or ketchup.

(12) The aimed product prepared by the process of the present invention in an amount of 40 to 80 parts by weight on a solid basis is mixed with 100 parts be weight of wheat flour and other components are added thereto, if required, to give a cooking material.

This cooking material may be in various forms such as a powder or a dough. In cooking, the product is formulated into a dough which finally comprises 200 to 500 parts by weight of moisture in total per 100 parts by weight of wheat flour. This dough may be molded into various shapes as such; laminated on other food material(s); introduced into other food material(s) in the form of a mass; or wrapped around or with other food material(s) followed by a thermal treatment such as roasting, boiling, steaming or frying to thereby give a cooked food which is palatable and has an excellent flavor and texture.

(13) The aimed product prepared by the process of the present invention in an amount of 0.1 to 15% (by weight; the same will apply hereinafter) on a solid basis is mixed with 45 to 90% of an edible vegetable oil, vinegar and water to give an oil-in-water type emulsion, which is then formulated into an emulsified product which is frequently similar to mayonnaise and sometimes to dressing. It is also possible in some cases to blend the above components in the preparation of the aimed product of the present invention to give the abovementioned ratio and then treat the obtained mixture with enzyme(s) and/or microorganism(s).

(14) The aimed product prepared by the process of the present invention in an amount of 0.1 to 5% (by weight; the same will apply hereinafter) on a solid basis is mixed with 10 to 45% of an edible vegetable oil, vinegar and water to give to oil-in-water type emulsion, which is then formulated into an acidic emulsified product which is frequently similar to salad dressing and sometimes to mayonnaise. It is possible in some cases to blend the above components in the preapration of the aimed product of the present invention to give the above ratio and then treat the obtained mixture with enzyme(s) and/or microorganism(s).

(15) The aimed product prepared by the process of the present invention in an amount of 0.1 to 40 parts by weight is mixed with 100 parts by weight of eggs and/or albumen. Other additives and/or food materials are further added to the mixture, if required. The resulting mixture is solidified by heating to thereby give a processed egg product such as fried egg, egg cake, pot-steamed hotchpotch, egg roll, omelet, tamago-dofu, custard pudding, pudding, custard or Bavarian.

(16) The aimed product prepared by the process of the present invention in an amount of 0.1 to 40% (by weight; the same will apply hereinafter) on a solid basis is mixed with 5 to 30% of fresh and/or synthetic cream, 5 to 30% of ground fish meat and common salt optionally with vegetable(s), fish meat fillets in the form of small blocks, seasoning(s) and other additive(s). Then the obtained mixture is solidified by heating to give a cooked food such as terrine, mousse or quenelle.

More particularly, the first step for the preparation of terrine comprises adding common salt to ground fish meat under milling; and then adding fresh and/or synthetic cream, milk, whole eggs and the aimed product of the present invention to the above mixture to give a farce. In the second step, vegetables, fish meat fillets in the form of small blocks, seasoning(s) and other additive(s) are added to the farce as obtained above, if required, and the resulting mixture is introduced into a container and steamed as such in an oven at 150° to 200° C. for 15 to 30 minutes. After cooling, the aimed terrine is obtained.

The preparation of mousse may be carried out as follows. Common salt is added to ground fish meat under milling followed by albumen and, if required, vegetable(s), fish meat fillets in the form of small blocks, seasoning(s) and other additive(s). Then fresh or synthetic cream and the aimed product of the present invention are added thereto and the mixture is kneaded until it becomes homogeneous. Then it is introduced into a container and steamed as such in an oven at 150° to 200° C. for 15 to 30 minutes to thereby give the aimed mousse.

The preparation of quenelle may be carried out as follows. As a preliminary treatment, a panade is made from milk, butter, wheat flour and whole eggs. Common salt is added to ground fish meat under milling. Then the aimed product of the present invention is added thereto optionally together with vegetable(s), fish meat fillets in the form of small blocks, seasoning(s) and other additive(s). Subsequently the above panade and fresh or synthetic cream are further added thereto and the resulting mixture is kneaded until it becomes homogeneous.

After the completion of the kneading, the mixture is molded and cooked in boiling water to give the aimed quenelle.

(17) The aimed product prepared by the process of the present invention is added at any step in the preparation of a flowable food to give, for example, various potage soups, grated soups, Chinese corn soup, weaning foods and flowable foods for sick or aged person. These flowable foods range from those which are relatively clear and have a low viscosity to highly viscous and semiflowable ones.

(18) The aimed product prepared by the process of the present invention in an amount of 0.1 to 40 parts by weight on a solid basis is mixed with 100 parts by weight of meats such as fish meat, chicken, beef, pork, mutton or whale meat. Further additives such as seasoning(s), spice(s) and colorant(s) and/or animal or vegetable fat or oil source(s), animal protein source(s), vegetable protein source(s) and carbohydrate source(s) as described above as well as luxuries, vegetable(s), meat(s) and fish(es) are optionally added thereto. Thus processed meat products such as ham, sausage, bacon, corned beef, hamberger steak, fried meat cake, meat ball, chicken ball, minced meat ball, Chinese meat ball, shrimp ball, fish ball, kamaboko, chikuwa and materials for Japanese hotchpotch can be obtained.

(19) The aimed product prepared by the process of the present invention in an amount of 5 to 80 parts by weight, preferably 15 to 30 parts by weight, on a solid basis is mixed with 100 parts by wieght of soybean milk to thereby prepare tofu.

(20) The aimed product prepared by the process of the present invention in an amount of 10 to 80 parts by weight, preferably 50 to 200 parts by weight, on a solid basis is mixed with 100 parts by weight of a konjak powder to give konjak.

(21) The aimed product prepared by the process of the present invention in an amount of 20 to 500 parts by weight, preferably 50 to 200 parts by weight, is mixed with 100 parts by weight of ground fish meat to give a material for Western dishes such as terrine or quenelle.

(22) The aimed product prepared by the process of the present invention in an amount of 100 parts by weight is mixed with 50 to 150 parts by weight of ground fish meat, 10 to 50 parts by weight, on a dry basis, of vegetable protein and/or 20 to 50 parts by weight of eggs and the resulting mixture is heated to give a tofu-like product which contains 5 to 50% by weight, preferably 10 to 30% weight, of the aimed product of the present invention.

To further illustrate the present invention, and not by way of limitation, the following Examples will be given.

EXAMPLE 1

The trunks of red ternner crabs including the carapaces, gonads, branchiae digestive organs and residual meat were introduced into a gauze basket and immersed in boiling water for 30 minutes. Then the material was frozen by allowing the same to stand in a freezer at −25° C. for 20 hours. Subsequently it was ground with a chopper and milled in a mass-colloider (mfd. by Masuko Sangyo) initially to give a grinder clearance of 10 mm and then to give that of 3 mm. Thus the crab material including the carapaces and trunks was milled to give a particle size of 100μ or below. Cooling water was passed through the mass-colloider as much as possible to thereby maintain the material temperature at approximately 30° C.

The crab meat thus milled was yet somewhat rough and gave a poor flavor. Thus 30 kg of the milled composition comprising the crab meat in the form of a slurry was introduced into a Stefan UP 12 (mfd. by Stefan) wherein hot water (50° C.) was passed through the jacket to thereby maintain the material temperature at 50° C. When the material temperature reached 50° C., of Amano A, which was a proteinase manufactured by Amano Pharmaceutical Co., Ltd., and 3 g of lysozyme, which would inhibit the growth of various bacteria, each dissolved in a small amount of water were added thereto.

After the completion of the addition, the milled composition was kneaded by stirring at a high speed for 30 minutes while maintaining the material temperature at 50°±2° C.

Then the water passed through the jacket was heated to 80° C. to thereby inactivate the proteinase. Then ice-cooled water was passed through the jacket to thereby lower the material temperature of the composition to 10° C.

Thus a proteinous material in the form of a brown paste containing 20% by weight of solid matters, which as the aimed product of the present invention, was obtained.

This brown pasty proteinousd material contained 45% of water-soluble proteins (in a solution of trichloroacetic acid) based on the total proteins and 2% of chitin.

The proteinous material as obtained above had excellent properties, a small viable count and a creamy texture. It was hardly rough and gave an enhanced sweet flavor characteristic of crabs. It was highly compatible with other food materials and did not lose the characteristics after thermally treated.

EXAMPLE 2

The shoulders of red ternner crabs, from which the carapaces, gonads, branchiae and digestive organs had been removed, were immersed in boiling water for 30 minutes. Then the material was cooled and frozen by allowing the same to stand in a freezer at −30° C. for 16 hours. Subsequently the frozen material was ground with a chopper and milled with a mass-colloider (mfd. by Masuko Sangyo) at a grinder clearance of 3 mm. Thus the crab material was formulated into particles of 150μ below in size. Then the material was further milled while adjusting the grinder clearance of the mass-colloider to 3 mm and passing cooling water through the jacket to thereby maintain the material temperature below 30° C. The milled crab meat thus obtained was yet rough and had a poor flavor. Thus 30 kg of the milled composition comprising the crab meat in the form of a slurry was introduced into a Stefan UM 12 (mfd. by Stefan) and stirred therein at a low rate. 15 g of Pronase (a protease mfd. by Kaken Pharmaceutical Co., Ltd.), 15 g of pancreation (mfd. by Difco) and 3 g of lysozyme, which would inhibit the growth of various bacteria, each dissolved in a small amount of water were added thereto.

After the completion of the addition, water at 50° C. was passed through the jacket of the Stefan UM 12 and the content was kneaded by stirring at a high rate while maintaining the material temperature of the composition at 50°±2° C. for 20 minutes.

Then the water passed through the jacket was heated to 80° C. to thereby inactivate the protease. Subsequently cooling water was passed through the jacket to thereby lower the material temperature of the composition to 10° C.

Thus a proteinous material in the form of a red paste containing 20% by weight of solid matters, which was the aimed product of the present invention, was obtained.

This red pasty proteinous material contained 35% of water-soluble proteins, based on the total proteins, in a solution of trichloroacetic acid and 1.3% of chitin.

The proteinous material as obtained above had excellent properties, a small viable count, and a creamy texture. It was highly compatible with other food materials, did not lose the characteristics after thermally treated and was hardly rough.

EXAMPLE 3

The shoulders of red ternner crabs, from which the carapaces, gonads, branchiae and digestive organs had been removed, were immersed in water containing 3% of hydrogen peroxide and 1% of sodium ascorbate. The temperature of the water was elevated to 50° C. and the immersion was continued for one hour to thereby inactivate discoloring enzymes as well as other harmful enzymes. Then 0.01% of catalase was gradually added thereto under slowly stirring to thereby decompose the hydrogen peroxide. When no qualitative reaction of hydrogen peroxide was observed, the composition was drained, thoroughly washed with cooling water and frozen in a freezer at −25° C. The frozen trunks of red ternner crabs were then ground with a chopper and milled with a mass-colloider while adjusting the grinder clearance to 3 mm and maintaining the material temperature of the composition below 30° C. by passing cooling water through the jacket. The milled crab meat thus obtained was uet rough and had a poor flavor. Thus 30 kg of the milled composition comprising the crab meat in the form of a slurry was introduced into a Stefan UM 12 (mfd. by Stefan) and treated in the same manner as the one described in Example 1.

Thus a proteinous material in the form of a while paste containing 20% by weight of solid matters, which was the aimed product of the present invention, was obtained.

This white pasty proteinous material contained 30% of water-soluble proteins, based on the total proteins, in a solution of trichloroacetic acid and 1.0% of chitin.

The proteinous material as obtained above had excellent properties, a small viable count and a creamy texture. It was highyl compatible with other food materials, did not lose the characteristics after thermally treated and was hardly rough.

EXAMPLE 4

Five parts of *Pandalus borealis* (pink shrimp) heads were mixed with five parts of krills, and the mixture was immersed in boiling water for 30 minutes. After draining and cooling, the composition was frozen by allowing the same to stand in a freezer at −25° C. for 20 hours. Then it was treated in the same manner as the one described in Example 1.

Thus a proteinous material in the form of a reddish brown paste containing 20% by weight of solid matters and having a shrimp-like flavor, which was the aimed product of the present invention, was obtained.

This proteinous material, which was in the form of a reddish brown paste and had a shrimp-like flavor, contained 42% of water-soluble proteins, based on the total proteins, in a solution of trichloroacetic acid and 0.7% of chitin.

The proteinous material as obtained above had excellent properties, a small viable count and a creamy texture. It was highly compatible with other food materials, did not lose the characteristics after thermally treated and was hardly rough.

EXAMPLE 5

PREPARATION OF SLICED CRAB PRODUCT 600 g of the proteinous material as prepared in Example 1, which as in the form of a brown paste, 150 g of casein sodium, 250 g of refined soybean oil, 20 g of sodium tartrate, 6 g of xanthan gum, 10 g of common salt, 1 g of sodium glutamate, 1 g of pepper and 2.0 g of a crab flavoring were introduced into an emulsifying pot (mfd. by Ohe Seisakusho Co., Ltd.) and stirred therein at a low rate while directly injecting vapor into the jacket and the pot in vacuo. When the internal temperature reached 50° C., the stirring was effected at a high rate and the injection of the vapor into the pot was ceased. Then the stirring at a high rate was continued until the internal temperature reached 80° C. When the internal temperature reached 80° C., the injection of the vapor into the jacket and evacuation were ceased and the molten content in the emulsifying pot was transferred to a stainless bucket.

While the product was still hot, it was placed on a wrapping film in the form of a stick and wrapped with the film. After formulating the product into a palte of 2 mm in thickness, the wrapped material was cut into square pieces, folded and cooled in a refrigerator. Thus a sliced crab product similar to a sliced cheese product was obtained.

When employed in, for example, sandwiches, this product gave an excellent crab flavor and a smooth texture.

EXAMPLE 6

PREPARATION OF STICK CRAB PRODUCT 300 g of the proteinous material in the form of a white paste as prepared in Example 3, 700 g of ground codfish meat and 2 g of common salt were thoroughly kneaded in a Robot coupe (mfd. by Robot coupe) at 10° C. or below. Then the kneaded mixture was extruded into boiling water through a nozzle having a mesh-type tip to give a fibrous composition. Separately 500 g of the proteinous material in the form of a white paste as prepared in Example 3, 500 g of ground codfish meat, 2 g of common salt and 0.01 g of red crab colorant were kneaded in a Robot coupe (mfd. by Robot coupe) at a material temperature of 10° C. or below. The kneaded composition was spreaded on a moist cloth in a thickness of approximately 3 mm. Then the fibrous composition as prepared above was placed thereon and rolled therewith. Thus a stick product wherein the fibrous composition was rolled with the red composition was prepared. Then the stick product was steamed as such in a steamer at the boiling temperature for approximately 30 minutes. After the completion of the steaming, it was cooled to give a stick crab product which contained 30 to 40% of crab meat and showed not roughness but a smooth texture.

EXAMPLE 7

PREPARATION OF SPAGHETTI 130 g of the proteinous material in the form of a reddish brown paste as prepared in Example 4, 300 g of semi-viscoelastic wheat flour, 3 g of common salt 10 g of gluten and 5 g of lecithin were mixed together in a mixing tank of a test noodle-making machine to such an extent that lumps were formed by intensely grasping with a hand. Then the resulting mixture was compressed twice or thrice while adjusting the roll clearance of the noodle-making machine at 5. Thus the powdery mixture was converted into a strap. Then this strap was folded to give a two-layer structure and then the above procedure was repeated three or four times while adjusting the clearance at 6. Finally, the compression was repeated twice at a clearance of 4 to thereby give a strap composition. The obtained strap composition was then passed through a tooth cutter of 3 mm×3 mm in width to thereby give spaghetti of 3 mm square.

The obtained spaghetti was boiled and fried in a conventional manner and crab meat was placed thereon. After sampling, the spaghetti was not rough but smooth and appropriately elastic and gave an excellent crab flavor.

EXAMPLE 8

The trunks of red turner crabs including the carapaces, gonads, branchiae, digestive organs and meat remaining in the trunks were treated in the same manner as the one described in Example 1 to give a milled composition, i.e., a crab meat slurry. 10 kg of this milled composition was sterilized with a high-pressure sterilizer at 120° C. for three seconds and introduced into a Stefan UM 12. Separately *Streptococcus lactis* and *Lactobacillus bulgaricus,* both provided by Fermentation Institute of Osaka University, had been cultivated together in a milk medium. 1 kg of the cocultivation liquor thus obtained was introduced into the Stefan UM 12 followed by 5 g of a proteinase "Amano A" (mfd. by Amano Pharmaceutical Co., Ltd.) dissolved in a smaller amount of sterilized water.

After the completion of the addition, hot water at 45° C. was passed through the jacket to thereby maintain the material temperature of the milled composition at 45°±2° C. and the mixture was kneaded under stirring at a low rate for three hours. Then the temperature of the water running through the jacket was elevated to 95° C. and this temperature was maintained for 30 minutes, thus inactivating the proteinase and lowering the lactic acid bacterial count. Subsequently ice/water was passed through the jacket to thereby lower the material temperature to 10° C.

Thus a proteinous material in the form of a somewhat aromatic brown paste containing 20% by weight of solid matters, which was the aimed product of the present invention, was obtained.

This proteinous material, which was in the form of a brown paste, contained 45% of water-soluble proteins in a solution of trichloroacetic acid based on the total proteins and 2.4% of chitin.

EXAMPLE 9

The trunks of red turnner crabs including the carapaces, gonads, branchiae, digestive organs and meat remaining in the trunks were introduced into a gauze basket and immersed in boiling water for 30 minutes. Then the composition was cooled and frozen in a freezer at −25° for 20 hours. Subsequently it was ground with a chopper and milled in a mass-colloider (mfd. by Masuko Sangyo) first at a grinder clearance of 10 mm and then at 3 mm thereof. Thus the composition including the carapaces and trunks of the crabs was milled to give a particle size of 100μ or below. During this treatment, the material temperature was maintained at approximately 30° C. by passing cooling water through the mass-colloider.

The crab meat thus milled was yet somewhat rough and gave an unsatisfactory flavor. 20 kg of this milled composition in the form of a crab meat slurry was introduced into a Stefan UM 12 (mfd. by Stefan) together with 5 kg of soybean protein and 5 kg of corn starch. Water at 50° C. was passed through the jacket to thereby maintain the material temperature at 50° C. When the material temperature reached 50° C., 20 g of a proteinase "Amano A" (mfd. by Amano Pharmaceutical Co., Ltd.) and 3 g of lysozyme, which wold inhibit the growth of various bacteria, each dissolved in a small amount of water were added thereto.

After the completion of the addition, the milled composition was stirred at a high rate while maintaining the material temperature thereof at 50°±2° C. Then the temperature of the water passed through the jacket was elevated to 95° C. to thereby inactivate the proteinase. Subsequently ice/water was passed through the jacket to thereby lower the material temperature of the composition to 10° C.

Thus a proteinous material in the form of a pale brown and viscous paste containing 40% by weight of solid matters, which was the aimed product of the present invention and contained carbohydrates, was obtained.

This proteinous material containing carbohydrates, which was in the form of a pale brown and viscous paste, contained 25% of water-soluble proteins, in a solution of trichloroacetic acid, based on the total proteins and 1.4% of chitin.

EXAMPLE 10

PREPARATION OF DRINK 100 of the proteinous material as prepared in Example 3 was introduced into a beaker and 300 g of water, 15 g of sucrose and 1 g of xanthan gum were added thereto. Then the resulting mixture was stirred in a homomixer and pasteurized at 145° C. for three seconds followed by cooling to 10° C. After adding an appropriate amount of a milk flavor thereto, a drink which had an appearance similar to that of milk and a delicious milky flavor was obtained.

EXAMPLE 11

PREPARATION OF DRINK 100 g of the proteinous material as prepared in Example 2 was introduced into a beaker. Then 3 g of gum arabic, 1 g of low-viscosity CMC, 30 g of sucrose and 0.5 g of citric acid dissolved in 100 g of water were added thereto. The resulting mixture was homogenized in a homomixer. In the solution thus obtained, 10 g of corn oil was emulsified at a high rate and 200 g of water was further added thereto. After homogenizing, the mixture was pasteurized at 100° C. for 30 minutes and then cooled to 40° C. Then an appropriate amount of an orange essence was added thereto to give a milky drink which had an orange flavor.

EXAMPLE 12

PREPARATION OF DRINK 100 g of the proteinous material as prepared in Example 2 was introduced into a beaker and 360 g of water, 40 g of a fructose/glucose solution, 0.2 g of tartaric acid and 1 g of xanthan gum were added thereto. Then the resulting mixture was homogenized and 15 g of an extract of Japanese plum was added thereto. Thus a drink which was suitably sour and had a flavor of Japanese plum was obtained.

EXAMPLE 13

PREPARATION OF DRINK 100 g of the proteinous material as prepared in Example 1 was introduced into a beaker and 300 g of water, 15 g of sucrose and 2 of CMC were added thereto. The resulting mixture was stirred in a homomixer and 300 g of soybean milk was further added thereto. Thus a drink of a delicious flavor, which had been never observed hitherto, was obtained.

EXAMPLE 14

PREPARATION OF DRINK 100 g of the proteinous material as prepared in Example 3 was introduced into a beaker and 300 g of water, 15 g of sucrose and 2 g of xanthan gum were added thereto. The resulting mixture was stirred in a homomixer and 200 g of milk was further added thereto. Thus a drink which had an excellent flavor similar to that of milk was obtained.

EXAMPLE 15

PREPARATION OF DRINK 100 g of the proteinous material as prepared in Example 3 was introduced into a beaker and 3 g of gum arabic, 30 g of sucrose and 0.5 g of citric acid dissolved in 100 g of water were added thereto. After stirring the resulting mixture in a homomixer, 10 g of corn oil was emulsified therein at a high rate. Then 200 g of water was added thereto to give a homogeneous composition and 100 g of orange juice was further added thereto. Thus a milky drink having an orange flavor was obtained.

EXAMPLE 16

PREPARATION OF DRINK 100 g of the proteinous material as prepared in Example 1 was introduced into a beaker and 360 g of water, 40 g of a fructose/glucose solution, 0.5 g of xanthan gum and 3 g of CMC were added thereto to give a homogeneous mixture. Then 200 g of vegetable juice was further added thereto to give a drink having an excellent flavor.

EXAMPLE 17

PREPARATION OF DRINK 100 g of the shoulders of red ternner crabs, which had been roughly ground to give a particle size of 100μ or below, was thawed and 3.0 g of common salt and 0.2 g of sodium pyrophosphate were added thereto. The resulting mixture was kneaded in a mill equipped with a jacket for controlling temperature and a stirrer to give a gelatinized composition. Hot water was passed through the jacket to thereby elevate the material temperature of the composition to 50° C. Then 0.05 g of a proteinase "Amano A" (mfd. by Amano Pharmaceutical Co., Ltd.) and 50 ppm of lysozyme, which was used as a growth inhibitor of various bacteria, each dissolved in a small amount of water were added thereto. After the completion of the addition, the kneading was continued for 15 minutes by stirring the composition at a high rate at 50° C. 15 minutes thereafter, 10 g of skim milk powder was immediately added thereto and the stirring was continued for additional 15 minutes. Then the temperature of the jacket was immediately elevated to 80° C. and this temperature was maintained for 30 minutes to thereby inactivate the enzyme. Then water was added to the gelatinous composition to give a solid content of 9 to 10% and the obtained mixture was stirred in a homomixer, pasteurized at 90° to 95° C. for five minutes and cooled to 37° C. Subsequently 3% of a starter mixture comprising *Lactobacillus bulgaricus* and *Streptococcus thermophilus*, which had been previously cultivated, was added thereto and the composition was fermented in a thermostat at 37° C. for six hours. Separately, 5% of sucrose, 3% of an asparagus juice and 0.2% of ascorbic acid were mixed together and pasteurized. The mixture thus obtained was homogenized together with the above fermented composition in a homomixer, cooled and pipetted into sterilized containers. Thus a refreshing drink which showed stable and excellent growth of bacteria was obtained.

EXAMPLE 18

PREPARATION OF DRINK 100 g of the shoulders of red ternner carbs, which had been roughly ground to give a particle size of 100μ or below, was thawed and introduced into a mill equipped with a jacket for controlling temperature and a stirrer wherein the material was heated to 50° C. while stirring. Then 3% of refined fish oil containing 20% of eicosapentaenoic acid, 0.5% of α-tocopherol and 5% of powdery yoghurt obtained by spray-drying were added thereto. To the resulting mixture, water was slowly added under stirring at a high rate to thereby give a solid content of 9 to 10%. Then 0.05 g of a proteolytic pronase (mfd. by Kaken Pharmaceutical Co., Ltd.), 0.05 g of a proteinase "Amano A" (mfd. by Amano Pharmaceutical Co., Ltd.) and 50 ppm of lysozyme, which was employed as a growth inhibitor of various bacteria, each dissolved in a small amount of water were added thereto. After the completion of the addition, the kneading was continued by stirring the mixture at a high rate at 50° C. for 15 minutes. 15 minutes thereafter, 10 g of skim milk powder was added thereto and the stirring was continued at 50° C. for additional 15 minutes. Then the temperature of the jacket was immediately elevated to 80° C. and this temperature was maintained for 30 minutes to thereby inactivate the enzymes. Separately, 3 g of asparagus juice, 0.2 g of ascorbic acid and 0.5 g of citric acid were mixed together and pasteurized. The mixture thus obtained was homogenized together with the above mixture decomposed with the enzymes in a homomixer. The obtained composition was then pasteurized at 95° C. for five minutes, cooled and pipetted into sterilized containers. Thus a refreshing drink showing excellent emulsification was obtained.

EXAMPLE 19

PREPARATION OF PETIT BREAD 10 g of green yeast was dissolved in 40 cc of tepid water. Separately a large spoonful of skim milk, a large spoonful of sugar and ⅔ small spoonful of common salt were added to 50 cc of tepid water and mixed therein. These two mixtures were mixed together with 60 g of the proteinous material as prepared in Example 2 and ½ egg. The resulting mixture was added to 200 g of highly viscoelastic wheat flour and the obtained mixture was kneaded. After adding a large spoonful of butter, the mixture was further doughed and fermented at 130° C. for 40 to 50 minutes. After punching, the dough was divided into six to eight portions and each portion was rounded, aged, molded into leaf shape, fermented on a hot plate at 38° C. for 40 minutes and finally baked in an oven at 180° to 190° C. for 13 minutes.

Thus a delicious petit bread which had a preferable appearance, a nice smell, and an excellent flavor was obtained.

EXAMPLE 20

PREPARATION OF CAKE 175 g of less viscoelastic wheat flour, a small spoonful of cinnamon, a small spoonful of sodium bicarbonate and ½ small spoonful of baking powder were mixed together. Separately, 150 cc of salad oil and 140 g of sugar were thoroughly mixed by means of a whisk in a container and two eggs and 140 g of the proteinous material as prepared in Example 4 were further added thereto and thoroughly stirred. These two mixtures were combined together and thoroughly mixed. Then the cake dough thus obtained was poured into a mold, on which an oil was applied and flour was sprayed, and baked in an oven at 160° C. for 40 to 60 minutes.

Thus a cake having a nice smell and an excellent flavor was obtained.

EXAMPLE 21

PREPARATION OF COATING OF CREAM PUFF 90 cc of water and 35 g of butter were introduced into a pot and heated. When the mixture boiled, 60 g of less viscoelastic wheat flour was added thereto and the mixture was quickly stirred. When a smooth mass was formed, the heating was ceased and 30 g of the proteinous material as prepared in Example 4 and two eggs were added thereto and the obtained mixture was stirred until it became viscous. Then the dough thus obtained was placed by portions on a hot plate, on which a small a mount of an oil was applied, with a spoon and baked in an over at 200° C. for ten minutes. After the dough was colored, the oven temperature was lowered to 180° C. and the baking was continued for 5 additional eight minutes.

Thus a coating for a cream puff having a preferable appearance, a nice smell and an excelent flavor was obtained.

EXAMPLE 22

PREPARATION OF CREPE

A large spoonful of sugar and 30 g of butter were added to 350 cc of milk and the mixture was heated to 50° to 50° C. Separately two eggs, 100 g of less viscoelastic wheat flour and 50 g of the proteinous material as prepared in Example 4 were thoroughly mixed together and the mixture as prepared above was added thereto by portions and thoroughly mixed. After straining, the mixture was covered with a well squeezed moist cloth and allowed to stand for 30 to 60 minutes. Then it was roasted in a drying pan.

Thus a crepe which had a preferable appearance, a characteristic flavor, a nice smell and an excellent taste was obtained.

EXAMPLE 23

PREPARATION OF OKONOMI-YAKI 150 g of less viscoelastic wheat flour, ¾ cup of water and a small amount of common salt were thoroughly mixed together. Then an egg and 100 g of the proteinous material as prepared in Example 1 were added thereto and the resulting mixture was roasted on a hot plate. After placing cabbage and Welsh onion slices, dried shrimps and green lever thereon, the residual dough was further placed thereon and the obtained product was turned over and further roasted.

The okonomi-yaki thus obtained had a preferable appearance, a nice smell and an excellent flavor.

EXAMPLE 24

PREPARATION OF CHINESE FRIED CAKE

To 50 g of the proteinous material as obtained in Example 4, two large spoonfuls of sugar, a small spoonful of salad oil and 50 cc of tepid water were added and thoroughly mixed. Then 100 g of less viscoelastic wheat flour was added thereto and the obtained mixture was thoroughly kneaded. The dough was covered with a well squeezed moist cloth and allowed to stand for approximately 30 minutes. The dough thus obtained was spread with a rolling pin to give a thickness of 5 mm. Then it was cut into strings of 8 m is width and 15 cm in length. Two of these strings were twisted together and fried in an oil at 170° C. for four to five minutes. Thus a Chinese fried cake which had a preferable appearance, a nice smell and an excellent flavor was obtained.

EXAMPLE 25

PREPARATION OF BREAD CRUMBS

To 200 g of highly viscoelastic wheat flour, 4 g of common salt, 10 g of sugar, 4 g of skim milk powder dissolved in 60 cc of hot water and 20 g of the proteinous material as prepared in Example 2 were added. The obtained mixture was kneaded while 4 g of yeast dissolved in 60 cc of tepid water, 0.2 g of yeast food and 10 g of shortening were further added thereto. After thoroughly kneaded, the resulting composition was fermented for approximately an hour at 30° C., punched, further fermented at 30° C. for approximately one hour and punched again. Subsequently the dough was baked in an oven at 200° C. for 20 minutes and the bread thus obtained was dried and ground.

Thus bread crumbs having an excellent flavor and a nice smell was obtained.

EXAMPLE 26

Preparation of cheese stick 250 g of sieved highly viscoelastic wheat flour was introduced into a container and 25 g of grated process cheese was added thereto and thoroughly mixed. Then a hollow was formed at the center of the obtained mixture and 13 g of green yeast dissolved in 50 cc of tepid water, a large spoonful of sugar and a small spoonful of common salt dissolved in 50 cc of tepid water and 50 g of the proteinous material as prepared in Example 1 were added thereto and kneaded. Finally 25 g of butter and 25 g of shorteing were added thereto and the obtained mixture was thoroughly kneaded. Then the composition was fermented at 30° C. for 40 to 60 minutes, punched, spread out to give a rectangle (10 cm × 25 cm) and divided into 10 to 12 portions with a skepper. After allowing to stand for 15 minutes, each portion was formulated into thin sticks, which were then folded, twisted, fermented on a hot plate at 36° to 38° C. for 40 minutes and baked in an oven at 190° C. for 15 to 20 minutes.

Thus a cheese stick having an extremely preferable appearance and a nice flavor was obtained.

EXAMPLE 27

Preparation of cracker 50 g of sieved wheat flour, 20 g of water, 0.2 g of yeast and 0.4 g of common salt were introduced into a container and thoroughly kneaded therein and the resulting dough was fermented at 30° C. for ten hours.

150 g of wheat flour was introduced into another container and 25 g of shortening was thoroughly incorporated thereto. Then 1.5 g of common salt, 0.6 g of sodium bicarbonate and 40 g of the proteinous material as prepared in Example 1 were added thereto. After thoroughly mixing, the fermented dough as obtained above was added thereto and the resulting mixture was kneaded and fermented at 30° C. for four hours. Then the dough was spreaded out with a rolling pin to give a thickness of approximately 0.5 mm, cut into a rectangle (3 cm × 5 cm) and toasted at 270° C. for three minutes to give a cracker.

The cracker thus obtained had a preferable toasted color and a characteristic and excellent flavor.

EXAMPLE 28

Preparation of pie 100 g of butter was divided into pieces each as large as the tip of a thumb and quickly mixed with 100 g of wheat flour. Then 55 g of cold water, in which 1.5 g of common salt and 30 g of the proteinous material as prepared in Example 1 were dissolved and/or dispersed, was sprayed thereon by portions to prepare a dough. The resulting dough was covered with a well squeezed moist cloth and allowed to stand for five minutes. Then the dough was spread out with a rolling pin to give a rectangle while optionally applying wheat flour to hands. After folding in three twice, the dough was covered with a squeezed moist cloth again and allowed to stand for a while. Then it was cut into pieces (5 cm×5 cm) and baked at 200° C. The pie thus obtained had a preferable appearance and a characteristic and excellent flavor.

EXAMPLE 29

Preparation of tofu and abraage

To a soybean milk for the preparation of tofu containing approximately 3% of soybean protein, which had been prepared by a known method and stored at 80° C., 20 g of the proteinous material as prepared in Example 1 and 0.5 g of xanthan gum dissolved or dispersed in 50 g of water were added and the mixture was stirred until it became homogeneous. Then 3 cc of a solidifier obtained by dissolving 37 g of solid bittern in 180 cc of water was added thereto. After thoroughly stirring for 10 to 15 minutes, the comosition was poured into a solidifying box in which a cotton cloth was placed and pressed with a lid and stone. When the composition showed an appropriate hardness, it was taken out of the box as wrapped with the cotton cloth, immersed in water for two hours, and cut to give an appropriate size.

The tofu thus obtained had a characteristic flavor which had been never observed in conventional ones and an excellent texture.

The tofu thus obtained was sliced, drained by wrapping with a cloth and squeezing and then fried. The abraage thus obtained had an excellent color and flavor.

EXAMPLE 30

Preparation of spread

To 120 g of the proteinous material as prepared in Example 1, 2 g of casein sodium, 8 g of common salt, 10 g of mustard, 20 g of grated onions and a small amount of pepper were added and the obtained mixture was thoroughly stirred.

100 ml of safflower oil was added to the mixture under stirring to thereby roughly emulsify the same therein. Then the mixture was stirred in a homomixer (mfd. by Nippon Kako Co., Ltd.). Thus a spread type composition in the form of an emulsion was obtained.

This emulsified composition could be well spread out when applied on bread and had an excellent flavor.

EXAMPLE 31

Preparation of emulsified fat for incorporation 500 g of the proteinous material as prepared in Example 1, 3 g of skim milk powder and 1 g of lecithin were introduced into a beaker. Then 100 g of water was added thereto and the resulting mixture was stirred at a low rate in a homomixer (mfd. by Nippon Kako Co., Ltd.). After the completion of the mixing, 500 g of salad oil was slowly added thereto while the stirring was continued at a high rate. After the completion of the addition, the stirring was continued for additional five minutes. Thus a viscous emulsified composition was obtained.

140 g of this emulsified composition was introduced into a container of a small whipper and 100 g of less viscoelastic wheat flour, 100 g of sugar, 100 g of eggs, 1 g of common salt, 1 g of baking powder and 2 g of rum were added thereto. The resulting mixture was whipped at a high rate for two minutes to thereby give a cake dough.

The cake dough thus obtained was poured into a pound mold, on the internal surface of which a small amount of a fat or an oil was applied and wherein paper was placed, to an extent of eight-tenth and baked in an oven at approximately 170° C. for 40 minutes. Thus a pound cake was obtained.

This pound cake had an excellent flavor.

EXAMPLE 32

Preparation of emulsified fat for toppping or to be incorporated into wheat flour To 100 g of the proteinous material as prepared in Example 1, 60 g of salad oil was slowly added under stirring. Then the mixture was emulsified in a homomixer to thereby give an emulsified oil composition of the present invention.

This emulsified oil composition was applied on the surface of an unbaked bread or cookie. After baking, a product excellent in gloss, color and flavor was obtained.

10 g of the abovementioned emulsified oil composition and 1 g of common salt dissolved in 40 cc of hot water were added to 100 g of wheat flour and the resulting mixture was thoroughly kneaded. The obtained dough was covered with a moist cloth and allowed to stand for 30 minutes. Then a gyoza coating was prepared in a conventional manner and a gyoza was formed with the use of the same. The gyoza thus obtained had a preferable color and an excellent flavor.

EXAMPLE 33

Preparation of mochi 200 g of glutinous rice was washed with water, immersed in water overnight and maintained in a strainer. 60 g of the proteinous material as prepared in Example 2 was mixed with the glutinous rice as described above and the resulting mixture was steamed in a mochi-maker to give a mochi dough. $\frac{2}{3}$ of the mochi dough thus obtained was formulated into mochi pieces while the residual $\frac{1}{3}$ of the same was cut into squares, dried and fried. Both of these mochi products were delicious. In particular, the fried mochi was superior in smell and flavor to those containing no pasty product.

EXAMPLE 34

Preparation of arare 500 g of nonglutinous rice was washed with water, immersed in water day and night and the steamed. 50 g of the proteinous material as prepared in Example 4 was added thereto and the resulting mixture was kneaded in a homomixer. Then the obtained composition was spread in a mold to give a thickness of 4 cm, dried, cut into squares, dried again and toasted.

The arare thus obtained had a preferable appearance and an excellent flavor and texture.

EXAMPLE 35

Preparation of senbei

To 500 g of rice flour, 100 g of the proteinous material as prepared in Example 4 300 g of water were added. Then the resulting mixture was kneaded, divided into approximately 15-g portions and steamed. Subsequently, these portions were combined together and thoroughly kneaded again. After cooling, the dough was spread out with a rolling pin, stamped to give discs of 5 cm in diameter, dried are toasted.

Thus a senbei which had a nice smell, an excellent flavor and a preferable appearance and texture was obtained.

EXAMPLE 36

Preparation of udon

To 100 ml of water, a small spoonful (5 g) of common salt and 60 g of the proteinous material as prepared in Example 1 were added and thoroughly mixed.

To 300 g of well seived semi-viscoelastic wheat flour, the above mixture was added by portions while intensely kneading the resulting mixture. The dough thus obtained was rounded, covered with a moist cloth and allowed to stand for two hours. Then the dough was spread out while optionally spraying a powder thereon and cut into strings to thereby give a teuchi udon-like product. After boiling in a large amount of water and washing with water, the udon gave a smooth texture and an excellent flavor.

Further the above udon was dried to give dried noodles which also gave an excellent flavor when boiled.

EXAMPLE 37

Preparation of nouille 150 g of less viscoelastic wheat flour, 1.5 g of common salt, the yolk of one egg (18 g), 45 g of the proteinous material as prepared in Example 1 and ½ of whole egg were kneaded together and the resulting composition was allowed to stand with covering with a moist cloth for four hours. Then a powder was sprayed thereon and the dough was spread out to give a thickness of 2 mm and then cut into strings of 8 cm × 3 mm.

These strings were boiled in a large amount of hot water containing a small amount of common salt for three minutes followed by draining and washing with water. Then the boiled product was fried in a frying pan and seasoned with common salt, pepper and powdery cheese. Thus delicious nouilles were obtained.

EXAMPLE 38

Preparation of gnocchis 210 ml of milk and 50 g of butter were introduced into a pan and heated. When the mixture boiled, 150 g of well sieved, less viscoelastic wheat flour was added thereto at once. The resulting mixture was quickly stirred with a wooden scoop. When the mixture became a glossy mass, the heating was ceased and 80 g of the proteinous material as prepared in Example 2 and three eggs (150 g) were added thereto. After thoroughly mixing, 1 g of nutmeg, 20 g of grated cheese and a small amount of common salt were added thereto and the resulting mixture was kneaded and introduced into a squeezing bag equipped with a round tip.

Then the composition was extruded from the bag to give a length of 3 cm into boiling water containing a small amount of common salt. The product thus extruded was boiled for eight minutes and taken with a strainer when it came up to the surface. Subsequently it was fried in butter in a frying pan and seasoned with common salt, pepper and powdery cheese to give delicious gnocchis.

Alternately the extruded product was fried in an oil and seasoned with common salt, pepper and powdery cheese. Thus delicious gnocchis was also obtained.

EXAMPLE 39

Preparation of Chinese noodles

To 500 g of wheat flour, 100 g of the proteinous material as prepared in Example 2, 35 g of water and 6 g of brine were added to give a noodle dough. The obtained dough was allowed to stand for a while and then pressed and cut to give Chinese noodles.

The resulting Chinese noodles were allowed to stand day and night and a certain portion of the same was boiled and introduced into a container containing a hot soup which had been separately prepared. After sampling, it was found that the needles had a characteristic flavor, an excellent and smooth texture and a good taste.

EXAMPLE 40

Preparation of batter for frying (1) Eight prawns each weighing 25 g were stripped while remaining the tail and the internals thereof were removed. Then each prawn was cut from the ventral side at three or four points in order to prevent it from curving.

(2) An egg was beaten in one cup of cold water and 100 G of sieved wheat flour and 30 g of the proteinous material as prepared in Example 4 were added thereto. The resulting mixture was stirred not to make it too viscous, thus giving a batter.

(3) The prawns as described in (1) were coated with wheat flour and then with a sufficient amount of the batter as prepared in (2). They were further crumbed and fried in a sufficient amount of an oil at 180° C. with holding the tail of each prawn. When a prawn came up to the surface of the oil, it was turned over while spreading the batter thereon with chopsticks to thereby give a crispy fried prawn.

The fried prawn thus obtained was superior in flavor and taste to conventional ones and had an excellent texture.

EXAMPLE 41

Preparation of batter for frying (1) 220 g of wheat flour was sieved twice.

(2) The yolk of one egg (18 g) and common salt were introduced into a container and kneaded therein. Then the wheat flour and 30 g of the proteinous material as prepared in Example 2 were added thereto. Further milk was added thereto by portions and the resulting mixture was smoothly stirred.

(3) Salad oil was added to the composition as prepared in (2) and the mixture thus obtained was covered with a lamp film and allowed to stand for approximately two hours.

(4) 300 g of white meat fishes such as flatfish, flounder or halibut, from which the bones and skin had been removed, were sliced into a bite-size pieces and slightly seasoned with common salt and pepper.

(5) The albumen of one egg was introduced into a clean container and whipped hard. Then it was incorporated into the composition as prepared in (3) by portions to give a batter.

(6) A clean frying oil was heated to a moderate temperature and the fish pieces of (4) dried with a cloth were spitted, coated wit the batter of (5) and slowly fried in the oil while occasionally turning upside down to avoid scorching.

Thus a fritter of the white meat fish, which was superior in flavor and taste to conventional ones and had an excellent texture, was obtained.

EXAMPLE 42

Preparation of batter for frying (1) The calyxes of three eggplants were removed. Then each eggplant was cut lengthwise and then into sticks of 1 cm in length. The obtained sticks were lixiviated with water.

(2) From 300 g of a pumpkin, seeds were removed with a spoon and the resulting pumpkin was peeled in spots. Subsequently the pumpkin was cut into sticks of 1 cm in length similar to the eggplants.

(3) 100 of kidney beans were stringed and cut into two, if too long.

(4) The materials of (1) to (3) were dried with a cloth and slightly seasoned with common salt and pepper.

(5) Eggs, common salt, olive oil and water were introduced into a container and 175 g of wheat flour was sieved into the mixture. Further 25 g of the proteinous material as prepared in Example 1 was added thereto and mixed. Thus a batter was prepared.

(6) A frying oil was heated to a moderate temperature and the materials of (4) coated with the batter of (5) were introduced therein. These materials were fried well to give crispy products.

Thus Italian fried vegetables which were superior in flavor and taste to conventional ones and had an excellent texture were obtained.

EXAMPLE 43

Preparation of batter for frying (1) The yolk of one egg was combined with water as cold as possible to give a cup of a mixture, which was then thoroughly mixed.

(2) 220 g of less viscoelastic wheat flour was sieved twice to thereby incorporate air thereto and then added to the mixture of (1). 30 g of the proteinous material as prepared in Example 2 was further added thereto and the resulting mixture was slightly mixed. Thus a batter was obtained.

(3) Two pods of garden peas were stringed, coated with the above batter and fried in an oil at a somewhat low temperature.

(4) Two ginger plants were cut to give stems of 7 to 8 cm, which were the cut crosswise. Two pickled ginger slices were coated and these materials were fried following the garden peas.

(5) One or two clusters of a broccoli were coated and fried at 180° C.

(6) After removing the internals and heads, two sardines were opened from the ventral side, slightly coated with wheat flour, coated with the batter and fried at 180° C.

Thus tempras which were much superior in taste and flavor to conventional ones and had an excellent texture were obtained.

EXAMPLE 44

Preparation of sauce veloute 30 g of butter was molten in a pot and 35 g of less viscoelastic wheat flour was added thereto and quickly fried therewith until it was colored. Then 80 g of the proteinous material as prepared in Example 2 dissolved in 500 cc of water was slowly added thereto and the resulting mixture was homogenized by quickly stirring.

A small amount of pepper and one laurel leaf were added thereto and the mixture thus obtained was cooked with small flames for 30 to 35 minutes with stirring.

Thus a sauce veloute of an excellent and characteristic flavor was obtained.

EXAMPLE 45

Preparation of white sauce 20 g of butter was molten in a pot and 25 g of less viscoelastic wheat flour was added thereto and fried therewith for one to two minutes without causing scorching. Then 200 cc of hot milk was slowly added thereto with thoroughly stirring in such a manner as to make no dumpling. Subsequently the proteinous material was prepared in Example 3 dissolved in 100 cc of a soup was added thereto followed by 1 g of common salt and a small amount of pepper. After the mixture boiled, it was cooked with small flames for 30 minutes.

Thus a white sauce having an excellent and characteristic flavor was obtained.

EXAMPLE 46

Preparation of sauce tartar

To 75 g of mayonnaise, 75 g of the proteinous material as prepared in Example 1 was added followed by ½ of a hard-boiled egg, 10 g of onion, 10 g of pickled cucumber, 2.5 g of parsely, each cut into pieces, and a small amount of mustard. After thoroughly mixing, a sauce tartar having an excellent and characteristic flavor was obtained.

With the use of mayonnaise and the proteinous material as prepared in Example 1, various sauces each having an excellent and characteristic flavor can be prepared by similar methods.

EXAMPLE 47

Preparation of sauce for spaghetti 25 g of onion and 10 g of carrot were cut into small pieces and fried with 10 g of molten butter in a pot for two to three minutes. Then 40 g of the proteinous material as prepared in Example 1 was added thereto followed by 10 g of wheat flour. The resulting mixture was further fried and 90 cc of water, 15 cc of tomato ketchup, 1.5 g of common salt and small amounts of pepper and synthetic seasoning(s) were added thereto. The mixture was concentrated with small flames to a volume of approximately ½ of the initial one.

Thus a sauce for spaghetti having an excellent and characteristic flavor was obtained.

EXAMPLE 48

Preparation of sauce for roast meat

To 100 ml of soy sauce, 20 g of the proteinous material as prepared in Example 4, 35 ml of mirin, 23 g of sugar, 2 g of sodium glutamate, 4 g of a seasoning composition, 0.3 g of pepper, 3.5 g of onion paste, 15 g of garlic puree and 30 cc of tepid water were added. When a homogeneous mixture was obtained, 4 g of soybean oil was added thereto and the mixture was homogenized in a homomixer.

Thus a sauce which had an excellent flavor and was suitable for, e.g., roast meat was obtained.

EXAMPLE 49

Preparation of janjan-men spread 150 g of the proteinous material as prepared in Example 1, 45 g of red miso, 16 g of soy sauce, 16 g of sugar and 100 cc of water were thoroughly mixed together. 45 g of an oil was heated in a pot and 28 g of a Welsh onion and 8 g of a ginger, each cut into small pieces, were fried therewith. When these vegetable began to smell spicy, the above mixture was added thereto and thoroughly mixed. After the resulting mixture boiled, it was concentrated with small flames until the oil separated out.

Thus the whole of the pork used in a conventional janjan-men spread was replaced with the proteinous material as prepared in Example 1. The janjan-men spread thus obtained had an excellent and characteristic flavor.

EXAMPLE 50

Preparation of cooking material

To 80 parts by weight of the proteinous material as prepared in Example 2, 20 parts by weight of wheat flour and a small amount of seasoning(s) were added. The resulting mixture was kneaded to give a homogeneous dough, which was then allowed to stand for a while before subjecting to the following cooking treatments.

(a) The dough was formulated into dumplings and introduced into boiling water.

(b) It was formulated into dumplings, each of which was spread out and roasted.

(c) It was formulated into dumplings, each of which was spread out, crumbed and fried.

(d) It was formulated into dumplings, each of which was spread out. Then vegetable fillings were wrapped therewith and steamed.

Every cooked product thus obtained had a characteristic flavor and texture similar to those of conventional ones and a preferable taste.

EXAMPLE 51

Preparation of cooking material

To 200 g of the proteinous material as prepared in Example 2, 300 g of wheat flour was added and thoroughly mixed. Further 20 g of mayonnaise was added thereto. The mixture thus obtained was molded into croguettes and fried at a moderate temperature until they were colored.

The cooked food thus obtained had an excellent flavor and texture.

EXAMPLE 52

Preparation of mayonnaise-like food 30 g of the proteinous material as prepared in Example 1, the yolk of one egg, ¼ small spoonful of common salt (1.5 g), and a small spoonful of vinegar were introduced into a well-washed container and the mixture was whipped therein. 150 ml of salad oil was added thereto under thoroughly stirring and two small spoonfuls of vinegar (10 ml) was finally added thereto to give an emulsified food similar to mayonnaise.

The addition of the proteinous material of the present invention thickened the flavor of each mayonnaise-like food and accelerated the emulsification thereof at the whipping and at the addition of the oil, which made the preparation process easy.

EXAMPLE 53

Preparation of mayonnaise-like food 20 g of the proteinous material as prepared in Example 2, 2 g of common salt, 3.0 g of seasoning(s), 2.0 g of spice(s) and 0.3 g of tamarind gum were dispersed and dissolved in 30 cc of water. To the obtained composition, 100 g of salad oil was slowly added and emulsified with a homomixer. Subsequently 30 g of vinegar was added thereto and the resulting mixture was emulsified. Thus an emulsified food of the present invention similar to mayon naise was obtained. The mayonnaise-like emulsified food thus obtained had a characteristic flavor and showed stable emulsification.

EXAMPLE 54

Preparation of emulsified food

The trunks of red turnner crabs were boild, roughly ground and milled to give a particle size of 100μ or below. 100 g of the crab material thus obtained, 30 g of vinegar and 0.1 g of Newlase (mfd. by Amano Pharmaceutical Co., Ltd.) dissolved in a small amount of water were introduced into a temperature-controlled homomixer, wherein the mixture was stirred at a high rate at 50° C. for 30 minutes. Then the mixture in the mixer was cooled to give a material temperature of 15° C. and 2 g of common salt, 1 g of CMC, 10 g of pepper and 10 g of ground onion were added thereto. While slowly adding 190 g of salad oil, the mixture was stirred at a high rate again to thereby give an emulsified food of the present invention similar to mayonnaise.

This emulsified food which had a smooth texture and an excellent flavor could be suitably employed in, for example, green salad.

EXAMPLE 55

Preparation of dressing-like food

Two small spoonfuls of mustard, 5 g of α-starch, ⅓ small spoonful of common salt, a small amount of pepper, 15 g of grated apply, 15 g of grated onion and 30 g of the proteinous material as prepared in Example 1 were introduced into a container and the resulting mixture was thoroughly stirred therein. After 8 ml of vinegar was added thereto, 90 ml of salad oil was further added thereto by portions under stirring to thereby emulsify therein. Finally 22 ml of vinegar was added thereto and the mixture was thoroughly mixed. Thus an emulsified food similar to a dressing was obtained.

The dressing thus obtained had a light flavor.

EXAMPLE 56

Preparation of dressing-like food 6 g of corn starch, 1.5 g of tapioca starch, 34 g of 5% apple vinegar, 8.0 g of sugar, 2.5 g of common salt and 20 g of water were heated and stirred together to give a starch paste. After cooling the paste, 40 g of the proteinous material as prepared in Example 4, 3.0 g of common salt, 10 g of sugar and 1.0 g of mustard powder were added thereto and homogeneously mixed.

Then salad oil was slowly added thereto while stirring in a homomixer. Thus an emulsified food of the present invention similar to a dressing was obtained.

The dressing-like food thus obtained had a characteristic and excellent flavor and showed a stable emulsification.

EXAMPLE 57

Preparation of dressing-like food

The trunks of red ternner crabs were boiled, roughly ground and milled to give a particle size of 100μ or below. 100 of this crab material, 30 g of vinegar and 0.1 g of Denaspin (mfd. by Nagase Co., Ltd.) dissolved in a small amount of water were introduced into a temperature-controlled mixer, wherein the mixture was stirred at a high rate at 50° C. for 30 minutes. Then the mixture in the mixer was cooled to give a material temperature of 15° C. 20 g of corn starch, 3 g of common salt, 5 g of pepper and 20 g of parsely pieces were added thereto and the resulting mixture was homogeneously mixed. Then the mixture was stirred at a high rate again while slowly adding 150 g of salad oil thereto. Thus an emulsified food of the present invention similar to a salad dressing was obtained.

The obtained dressing-like food which had a smooth texture and an excellent flavor was suitable for, e.g., green salad.

EXAMPLE 58

Preparation of terrine 500 g of frozen ground Alaska pollack meat (SA) was ground with a silent cutter while adding 10 g of common salt thereto. Five minutes thereafter, 1200 g of the proteinous material as prepared in Example 4, 600 g of whole eggs, 300 cc of milk and 800 cc of fresh cream were added thereto and the resulting mixture was kneaded for ten minutes. Thus 3710 g of a farce was obtained. To 1000 g of the farce thus obtained, 500 g of fresh salmon fillets in the form of small blocks, 2 g of common salt and 1 g of white pepper were added. After homogeneously mixing, the composition was introduced into a container and steamed as such in an oven at 170° C. for 20 minutes. After cooling, 1410 g of a terrine was obtained.

The terrine thus obtained had a satisfactory appearance, texture and flavor and was highly smooth and delicious.

EXAMPLE 59

Preparation of terrine 500 g of frozen ground Alaska pollack meat (SA) was ground with a silent cutter while adding 10 g of common salt thereto. Five minutes thereafter, 1200 g of the proteinous material as prepared in Example 1, 600 g of whole eggs, 300 cc of milk and 800 cc of fresh cream were added thereto and the resulting mixture was kneaded for ten minutes. Thus 3710 g of a farce was obtained. To 1000 g of the farce thus obtained, 500 g of boiled and drained spinach, 2 g of common salt and 1 g of white pepper were added. After homogeneously mixing, the composition was introduced into a container and steamed as such in an oven at 170° C. for 20 minutes. After cooling, 1410 g of a terrine was obtained.

EXAMPLE 60

Preparation of terrine 500 g of frozen groun Alaska pollack meat (SA) was ground with a silent cutter while adding 10 g of common salt thereto. Five minutes thereafter, 1200 g of the proteinous material as prepared in Example 1, 600 g of whole eggs, 300 cc of milk and 800 cc of fresh cream were added thereto and the resulting mixture was kneaded for ten minutes. Thus 3710 g of a farce was obtained. To 1000 g of the farce thus obtained, 500 g of boiled and strained carrots, 2 g of common salt and 1 g of white pepper were added. After homogeneously mixing, the composition was introduced into a container and steamed as such in an oven at 170° C. for 20 minutes. After cooling, 1410 g of a terrine was obtained.

The terrine thus obtained had a satisfactory appearance, texture and flavor and was highly smooth and delicious.

EXAMPLE 61

Preparation of mousse 200 g of frozen ground Alaska pollack meat (SA) and 100 g of water were ground with a silent cutter while adding 6 g of common salt thereto. Five minutes thereafter, 400 g of the proteinous material as prepared in Example 1 and 50 g of albumen were added thereto followed by 200 cc of fresh cream and 120 g of sea bream fillets in the form of small blocks. Then the resulting mixture was kneaded until it became homogeneous. The mixture was introduced into a container and steamed as such in an oven at 200 ° C. for 20 minutes. Thus 930 g of a mousse was obtained.

Ten panelists who took the mousse thus obtained with sauce americane highly evaluated the apperance, texture and flavor thereof.

EXAMPLE 62

Preparation of mousse 200 g of frozen ground Alaska pollace meat (SA) and 100 g of water were ground with a silent cutter while adding 6 g common salt therto. Five minutes thereafter, 400 g of the proteinous material as prepared in Example 2 and 50 g of albumen were added thereto followed by 200 cc of fresh cream and 120 g of sea bream fillets in the form of small blocks. Then the resulting mixture was kneaded until it became homogeneous. The mixture was introduced into a container and steamed as such in an oven at 200° C. for 20 minutes. Thus 930 g of a mousse was obtained.

Ten panelist who took the mousse thus obtained with sauce americane highly evaluated the appearance, texture and flavor thereof.

EXAMPLE 63

Preparation of mousse 200 g of frozen ground Alaska pollace meat (SA) and 100 g of water were ground with a silent cutter while adding 6 g of common salt thereto. Five minutes thereafter, 400 g of the proteinous material as prepared in Example 4 and 50 g of albumen were added thereto followed by 200 cc of fresh cream and 120 g of boiled and drained spinach. Then the resulting mixture was kneaded until it became homogeneous. The obtained mixture was introduced into a container and steamed as such in an oven at 200° C. for 20 minutes to give 930 g of a mousse. Ten panelist who took the mousse thus obtained with sauce americane highly evaluated the appearance, texture and flavor thereof.

EXAMPLE 64

Preparation of quenelle 200 cc of milk and 50 g of butter were heated in a pot until the butter was molten and the milk was ready to boil. Then 100 g of wheat flour was added thereto at once and the resulting mixture was vigorously mixed using a wooden spatula. After forming a dough mass, it was dried with medium flames with stirring until a thin film was formed on the bottom of the pot. Then the dough was transferred into a container and 100 g of beaten eggs were added thereto by portions while kneading the dough with the wooden spatula in such a manner as to cut the dough. Thus the eggs were smoothly mixed with the dough. The obtained panade was allowed to stand in a cold place. Separately 300 g of frozen ground Alaska pollack meat was ground with a silent cutter while adding 5.4 g of common salt thereto. Five minutes thereafter, 700 g of the proteinous material as prepared in Example 4, 200 g of small shrimp pieces, 450 g of the abovementioned panade and 200 cc of fresh cream were added thereto and thoroughly kneaded. After the completion of the kneading, the dough thus obtained was poured into a large amount of boiling water with a large spoon. When the dough which had been submerged under water came up to the surface, it was boiled as such for five minutes and then cooled in cold water.

15 panelists who took 1670 g of the quenelle with sauce americane evaluated the appearance, texture and flavor thereof as satisfactory.

EXAMPLE 65

Preparation of cream soup 30 g of butter was molten in a pot and 50 g of onion slices were freied therewith. Then 40 g of wheat flour was added thereto and the mixture was further fried for two to three minutes. Subsequently 150 g of the proteinous material as prepared in Example 2 dissolved in 1000 cc of water was added thereto. After boiling, the mixture was cooked with small flames for 30 to 40 minutes. Then the cooked product, which was ued as a base, was diluted with 200 cc of water and seasoned with small amounts of salt and pepper and 100 cc of fresh cream.

Thus a cream soup having a characteristic and excellent flavor was obtained.

EXAMPLE 66

Preparation of Chinese corn soup 50 g of the proteinous material as prepared in Example 1 was thoroughly mixed with a small amount of ginger juice and 10 cc of sake. 230 cc of a soup and 225 g of creamy sweet corn were heated in a pot and seasoned with common salt and sake. Then 5 g of potato starch dissolved in 200 cc of water was added thereto under stirring. Then the abovementioned mixture, to which slightly whipped albumen had been added, was added thereto and the mixture thus obtained was quickly stirred. When the albumen was cooked, the heating was ceased.

Thus a Chinese corn soup having an excellent flavor, wherein the taste of the proteinous material of the present invention well suited with that of the corn, was obtained.

EXAMPLE 67

Preparation of egg soup 400 cc of a stock was heated in a pot and seasoned with 6 cc of soy sauce and a small amount of common salt. Then 3 g of potato starch dissolved in 10 cc of water was added thereto. When the mixture became somewhat viscous, a mixture obtained by thoroughly mixing 20 g of the proteinous material as prepared in Example 1 with 50 g of a fresh egg was added thereto through a perforated spoon. Once the obtained soup boiled, the heating was ceased.

Thus an egg soup having an excellent flavor, wherein the taste of the proteinous material of the present invention well suited with that of the egg, was obtained.

EXAMPLE 68

Preparation of weaning food 30 g of the proteinous material as prepared in Example 2, 50 g of roughly drained grated Japanese raddish, 6 cc of soy sauce and 6 cc of mirin were added to 70 cc of a preliminarily formed stock in a pot. After covering the pot, the mixture was cooked with relatively small flames. When the mixture boiled, an egg may be dropped, if desired, to make the appearance of the food fine.

Thus a weaning food which had an excellent flavor of the proteinous material of the present invention and a smooth texture was obtained.

EXAMPLE 69

Preparation of rice gruel 150 cc of water or a stock was boiled in a pot and 50 g of cooked rice quickly washed with hot water was added thereto. During the cooking, a small amount of common salt and 30 g of the proteinous material as prepared in Example 4 were added thereto. The cooking was continued until no moisture was observed. Further miso or soy sauce may be added, if desired.

Thus a rice gruel having excellent flavor and viscosity inherent in the proteinouns material of the present invention was obtained.

EXAMPLE 70

Preparation of well-cooked udon 40 g of boiled udon was washed with running water to remove the sliminess. Then it was quickly washed with hot water and cut into pieces. Separately 10 g of spinach was thoroughly boiled, drained and cut into pieces. The abovementioned udon was well-cooked in 100 cc of a stock and 30 g of the proteinous material as prepared in Example 2 and the abovementioned spinach were added thereto. The resulting mixture was cooked for a short period and seasoned with 5 cc of soy sauce.

Thus well-cooked udon having an excellent flavor as well as the taste and viscosity inherent in the proteinous material of the present invention was obtained.

EXAMPLE 71

Preparation of hamburger steak 12 g of bread was finely milled and mixed with 15 g of the proteinous material as prepared in Example 1. Then 70 g of minced beef, 30 g of fried onion pieces, 12 g of egg, 1.2 g of common salt, a small amount of pepper and a small amount of a synthetic seasoning were added thereto. After thoroughly mixing, the mixture was formed into a flat ellipse and beaten to the palm of the left hand with the right hand several times to thereby harden the meat. After regulating the shape, it was roasted in a frying pan.

Thus a hamburger steak having excellent appearance and flavor was obtained.

EXAMPLE 72

Preparation of meat loaf 30 g of bread, 50 g of the proteinous material as prepared in Example 2, 300 g of minced beef, 30 g of an onion, 50 g of an egg. 4.4 g of common salt, a small amount of pepper and a small amount of a synthetic seasoning were mixed together in the same manner as the one described in Example 1. Then the obtained composition was made into a semicylindrical form of 5 cm in height on a moist cloth. Then it was transferred to a hot plate on which an oil had been applied. 8 g of butter was placed on the semicylindrical composition, which was then roasted at 180° C. for 25 minutes while pouring the oozing soup thereto to thereby make it glossy. Thus a meat loaf having excellent appearance and flavor was obtained.

EXAMPLE 73

Preparatin of kamaboko-like food 80 parts of frozen ground fish meat was milled at a material temperature of approximately −5° to −6° C. Then 2 parts of common salt was added thereto at approximately 1° C. and the mixture was further stirred. Subsequently 20 parts of the proteinous material as prepared in Example 3, 10 parts of starch, 2 parts of a seasoning, 2 parts of a vegetable oil, 10 parts of frozen albumen, 5 parts of sugar, 5 parts of mirin and 50 parts of water were added thereto and the resulting mixture was thoroughly stirred.

An appropriate amount of the mixture thus obtained was placed on a kamaboko-plate and allowed to stand in a retainer at 40° C. for 40 minutes. Then it was steamed at 98° C. for 40 to 70 minutes and then cooled.

Thus a delicious kamaboko having a soft texture different from that of a conventional one was obtained.

EXAMPLE 74

Preparation of fish sausage 1000 g of frozen ground meat (B grade) was ground with a silent cutter while adding 700 g of the proteinous material as prepared in Example 2, 200 g of lard, 200 g of gelatin, 70 g of common salt, 5 g of Poly Ami (a natural seasoning), 300 g of corn starch and a dye mixture comprising 2 g of a 1% solution of Food Red No. 106 and 0.8 og of a 1% soluion of Food Yellow No. 5 were added thereto. After thoroughly stirring, 80-g portions of the mixture were filled in casings and pasteurized in boiling water.

The fish sausage thus obtained had a smooth texture which was never observed in conventional ones.

EXAMPLE 75

Preparation of tofu 100 g of the proteinous material as prepared in Example 2 was added to 500 ml of water and thoroughly mixed therewith.

To the mixture thus obtained, 65 g of soybean milk powder was added by portions. Then the resulting mixture was heated under stirring in order to prevent it from scorching. After maintaining the material temperature at 80° to 95° C. for several minutes, the heating was ceased and 3 g of a solidifier (a glucono-δ-lactone preparation) was added and stirred. Then the mixture was quickly poured into an appropriate container and molded.

After sufficiently solidifying, the molded composition was taken out of the container and lixiviated with water, thus giving a tofu.

The tofu thus obtained was very delicious.

EXAMPLE 76

Preparation of tofu

To 500 ml of water, 100 g of the proteinous material as prepared in Example 4 was added simultaneously with 65 g of soybean milk powder by portions under slow stirring.

The resulting mixture was heated under stirring in order to prevent the same from scorching. After maintaining the material temperature at 80° to 95° C. for several minutes, the heating was ceased and 3 g of a solidifier (a glucono-δ-lactone preparation) was added thereto. Then the mixture was quickly poured into an appropriate container and molded.

After sufficiently solidifying, the molded composition was taken out of the container and lixiviated with water, thus giving a tofu.

The tofu thus obtained was very delicious.

EXAMPLE 77

Preparation of tofu

To 500 ml of water, 65 g of soybean milk powder was added by portions under slow stirring.

The obtained mixture was heated with stirring in order to prevent the same from scorching. After maintaining the material temperature at 80° to 95° C. for several minutes, the heating was ceased. Then 100 g of the proteinous material as prepared in Example 1 was added thereto and the mixture was thoroughly stirred. Subsequently 3 g of a solidifier (a glucono-δ-lactone preparation) was added thereto with stirring. Then the mixture was quickly poured into an appropriate container and molded.

After sufficiently solidifying, the molded composition was taken out of the container and lixiviated with water, thus giving a tofu.

The tofu thus obtained was very delicious.

EXAMPLE 78

Preparation of konjaku

To 350 ml of water, 70 g of the proteinous material as prepared in Example 2 was added and thoroughly mixed therewith.

Then 10 g of konjaku powder was added to the above mixture by portions under slow stirring. Then the mixture was covered and allowed to stand for one hour to thereby make the konjaku powder to sufficiently swell. Then the mixture was vigorously stirred while maintaining the material temperature at 70° to 80° C. to thereby sufficiently dissolve the konjaku powder. Subsequently 25 cc of a 2.5% calcium hydroxide solution was added thereto and the mixture was quickly stirred, poured into an appropriate container and molded.

After sufficiently solidifying, the molded composition was taken out of the container and heated in hot water at approximately 90° C. for 30 minutes or longer, i.e., lixiviated, to give a konjaku.

The konjaku thus obtained was delicious.

EXAMPLE 79

Preparation of konjaku

To 350 ml of water, 70 g of the proteinous material as prepared in Example 4 was added simultaneously with 10 g of konjaku powder by portions under slow stirring. Then the mixture was covered and allowed to stand for approximately one hour to thereby make the konjaku powder to sufficiently swell. Then the mixture was intensely stirred while maintaining the material temperature at 70° to 80° C. thereby sufficiently dissolve the konjaku powder. Subsequently 25 cc of a 2.5% calcium hydroxide solution was added thereto and the mixture was quickly stirred, poured into an appropriate container and molded.

After sufficiently solidifying, the molded composition was taken out of the container and heated in hot water at approximately 90° C. for 30 minutes or longer, i.e., lixiviated, to give a konjaku.

The konjaku thus obtained was delicious.

EXAMPLE 80

Preparation of konjaku

To 350 ml of water, 10 g of konjaku powder was added by portions under slow stirring. Then the mixture was covered and allowed to stand for approximately one hour to thereby make the konjaku powder to sufficiently swell. Then the mixture was intensely stirred while maintaining the material temperature at 70° to 80° C. to thereby dissolve the konjaku powder. Subsequently 70 g of the proteinous material is prepared in Example 1 was added thereto and thoroughly mixed therewith. To the obtained mixture, 25 cc of a 2.5% calcium hydroxide solution was added and the resulitng mixture was quickly stirred, poured into an appropriate container and molded.

After sufficiently solidifying, the molded composition was taken out of the container and heated in hot water at approximately 90° C. for 30 minutes or longer, i.e., lixiviated to give a konjaku.

The konjaku thus obtained was delicious.

EXAMPLE 81

Preparation of terrine

To 200 g of frozen ground fish meat, 200 g of the proteinous material is prepared in Example 2 was added and thoroughly mixed therewith by using, for example, Robot coupe.

After adding 0.5 g of common salt, the above mixture was thoroughly kneaded and 50 g of milk, 90 g of whole eggs, 120 g of fresh cream and a small amount of white pepper were added thereto. The resulting mixture was thoroughly stirred to give a homogeneous paste. Then the paste was poured into an appropriate terrine mold and steamed therein at 230° C. for 45 minutes to thereby give a terrine.

The terrine thus obtained had a soft and smooth texture without showing any elastic and rubbery texture, i.e., kamaboko-like texture, which was often observed in those prepared from frozen ground fish meat alone as a fish meat material.

EXAMPLE 82

Preparation of tofu-like food

To 100 g of separated soybean protein, 200 g of refined soybean oil and 400 g of water were added. The resulting mixture was thoroughly mixed and emulsified to thereby give a curd product.

To 100 g of frozen ground Alaska pollack meat, 100 g of the proteinous material as prepared in Example 1 was added. Then the mixture was thoroughly kneaded together with 2 g of common salt. Then 100 g of the curd product as described above was added thereto. To the resulting mixture, 50 g of alumben and 100 g of water were added and the obtained mixture was homogenized. After deaerating, the mixture was packed in a mold and steamed at 85° to 90° C. for 30 minutes to thereby give a tofu-like food.

The tofu-like food thus obtained had a white color and a smooth texture similar to kinugoshi-tofu. It was delicious when taken after either cooled or cooked in water.

EXAMPLE 83

Preparation of tofu-like product

To 100 g of separated soybean protein, 200 g of refined soybean oil and 400 g of water were added. The resulting mixture was thoroughly mixed and emulsified to thereby give a curd product.

To 100 g of frozen ground Alaska pollack meat, 100 g of the proteinous material as prepared in Example 4 was added. Then the mixture was kneaded together with 2 g of common salt.

Then 200 g of the curd product as described above was added thereto. To the resulting mixture, 50 g of albumen and 100 g of water were added and homogenized. The obtained mixture was packed into a mold and steamed therein at 85° to 90° C. for 30 minutes to thereby give a tofu-like food.

The tofu-like food thus obtained was similar to momen-tofu and delicious when taken after either cooled or cooked in water.

EXAMPLE 84

Preparation of omelet-like fried egg (tamago-yaki)

To 100 g of whole eggs, 2 g of the proteinous material as prepared in Example 1, 1 g of common salt, 20 g of water and 3 g of starch was added. After thoroughly stirring, the mixture was subjected to a conventional treatment for the preparation of omelet-like fried egg. The product thus obtained had a characteristic and light taste, which was never observed in conventional ones, and more delicious than those containing no paste product.

EXAMPLE 85

Preparation of Western-style pot-steamed hotchpotch

To 100 g of eggs, 200 g of fresh cream, 50 ml of white wine, 10 g of sugar and a small amount of garlic were added and the mixture was stirred in such a manner as not to form any foam. Then 50 g of canned crab flakes and 50 g of the proteinous material as prepared in Example 2 were added thereto. The mixture thus obtained was poured into five coffee cups and steamed therein at 100° C. for 15 minutes. Separately, 1 g of casein sodium, 40 g of salad oil and 100 g of the proteinous material as prepared in Example 2 were introduced into a container and stirred with a stirrer at a high rate to give a spread. The spread thus obtained was placed on the steamed product in the cups and lemon slices were further placed thereon together with a parsley.

The dough of the Western-style pot-steamed hotch-potch thus prepared had a smooth texture and the texture of the spread was also smooth. The flavor of the above product was more characteristic and better than that of those containing no porteinous material of the present invention.

EXAMPLE 86

Preparation of Bavarian cream 10 g of powdery gelatin and 50 ml of water were introduced into a pot and the gelatin was allowed to swell therein for ten minutes.

Then 60 g of sugar and 30 g of yolk were added thereto and stirred.

Separately 200 ml of milk and 50 g of the proteinous material as prepared in Example 2 were heated in another pot. Then the latter mixture was slowly added to the former one while heating with small flames was continued under stirring. When the yolk was heated, the heating was ceased and an appropriate amount of vanilla essence was added thereto. Then the mixture was cooled until it became viscous.

80 g of fresh cream and 10 g of sugar were introduced into a cold container and gently whipped while maintaining the mixture at 50° C. by cooling the bottom of the container with ice/water. When the fresh cream was gradually hardened, the viscous jelly as prepared above was added thereto and the obtained mixture was quickly stirred.

Then the Bavarian cream thus prepared was poured into a jelly mold, on the inside of which fresh salad oil was applied, and solidified therein by cooling. Then it was taken out of the mold and placed on a plate.

The Bavarian cream thus obtained showed no roughness but a mild and characteristic flavor which was superior to that of the one containing no proteinous material of the present invention.

EXAMPLE 87

Preparation of wine jelly 40 g of gelatin was softened by immersing in water and then drained. 1000 ml of water, the above gelatin, 210 g of sugar and three lemon slices were introduced into a pot and the mixture was heated with medium flames for 30 minutes while continuously stirring with a wooden scoop. (When boiled, the mixture was heated with small flames to thereby gently boil.)

To the sugar jelly thus obtained, 100 g of the proteinous material as prepared in Example 3, 60 ml of red wine and 20 ml of lemon juice were added and thoroughly stirred. Then the mixture was heated to such an extent as not to boil, with stirring.

Then the mixture was poured into ten jelly molds. After cooling, the content of each mold was taken out, placed on a plate and decorated with whipped cream.

The jelly thus obtained showed no roughness and had a smooth texture and an excellent crab flavor.

EXAMPLE 88

Preparation of custard pudding

To 45 g of the proteinous material as prepared in Example 2, 100 g of water and 10 g of sugar were added and the mixture was heated to 60° C.

Separately, 30 g of whole egg and 10 g of sugar were mixed in a container and the resulting mixture was slowly added to the above one with stirring. After adding a small amount of vanilla essence, the mixture was sieved and poured into pudding molds containing a small amount of caramel sauce at the bottom. These molds were placed on a plate, to which hot water was poured. Then the puddings were baked in an oven at 150° C.

The pudding thus obtained showed no roughness but a smooth texture and an excellent crab flavor.

EXAMPLE 89

Preparation of yoghurt 100 g of the proteinous material as prepared in Example 3, 100 g of water and 10 g of skim milk powder were mixed in a homomixer to give a somewhat viscous solution. Then the solution was heated to 50° C. and 16 g of sugar was added thereto and dissolved therein.

Then the solution was pasteurized at 100° C. for 30 minutes and then cooled to 37° C.

Then 5 g of a liquid culture, which had been obtained by cultivating *Streptococcus thermophilus*, *Streptococcus lactis* and *Lactobacillus bulgaricus* in a 10% solution of skim milk powder, was added to the above mixture. The resulting mixture was introduced into a sterilized yoghurt bottle, covered with a paper cap and fermented in a thermostat at 37° C. for seven hours. Then it was allowed to stand at 5° C. for 12 hours to thereby give a yoghurt having a smooth texture and an acidity of 0.8%.

EXAMPLE 90

Preparation of cheese-like product 130 g of the proteinous material as prepared in Example 1 was introduced into an Agi-homomixer (mfd. by Tokushu Kikako Co., Ltd.). A natural cheese mixture milled with a meat mincer comprising 25 g of cheddar cheese and 35 g of gouda cheese, 0.5 g of sodium polyphosphate and 0.2 g of sodium pyrophosphate, which were employed as fluxes, 0.4 g of a fungicide and a small amount of a cheese flavoring were added thereto and kneaded. After thermally melting the mixture at 80° C. under a pressure of 35 mmHg at a high rate, a paste mixture was prepared. Then the paste was poured into a mold and cooled to give a product which had a smooth texture similar to that of a commercially available process cheese.

EXAMPLE 91

Preparation of chesse spread 200 g of the proteinous material as prepared in Example 2 was introduced into an Agi-homomixer (mfd. by Tokushu Kikako Co., Ltd.). A natural cheese mixture milled with a meat mincer comprising 25 g of cheddar cheese and 25 g of gouda cheese, 0.3 g of sodium polyphosphate and 0.2 g of sodium pyrophosphate, which were employed as fluxes, 0.4 g of a fungicide and a small amount of a cheese flavoring were added thereto. After thermally melting the mixture at 80° C. under a pressure of 35 mmHg at a high rate, a paste mixture was obtained. Then the paste was poured into a mold and cooled to thereby give a product which had a smooth texture and palatability similar to that of commercially available cheese spread.

EXAMPLE 92

70 kg of the heads and waste portions of black tiger prawns and 30 kg of white prawns were mixed together and introduced into a tank, in which the mixture was steamed with vapor at 100° C. for 30 minutes.

Then the soup obtained by the steaming was mixed with shrimps and 5-kg portions of the resulting mixture were introduced into bread cases and frozen in a refrigerator at −25° C. for 20 hours.

Subsequently the frozen product was treated in the same manner as the one described in Example 1 to thereby give a reddish brown, pasty proteinous material containing 20% by weight of solid matters and having a prawn flavor.

The proteinous material thus obtained contained 37% by weight of water-soluble proteins, based on the total proteins, as determined by precipitating from a trichloroacetic acid solution and 1.2% by weight of chitin. This product had a significantly higher shrimp flavor and shrimp smell than conventional shrimp pastes did. It showed a small viable count, no roughness, although it contained the carapaces, and a creamy texture. It was highly compatible with other food materials and showed no roughness and did not lose its characteristics after thermally treated. When applied to liquid foods, it showed an emulsifiability and no roughness and did not precipitate after pasteurized. Thus an excellent drink could be prepared therefrom.

100 parts by weight of this proteinous material was mixed with 100 parts of enzymatically decomposed dextrin in a tank and the resulting mixture was spray-dried. Thus a shrimp powder having a characteristic flavor was obtained. This powder was highly soluble in water to give a smooth and homogeneous paste.

EXAMPLE 93

The shoulders of red ternner crabs, from which the carapaces, gonads, branchiae and digestive organs had been removed, were treated in the same manner as the one described in Example 1 to give a milled crab meat in the form of a slurry.

40 kg of the crab meat slurry thus obtained was mixed with 4 kg of casein sodium and the resulting mixture was heated to 50° C. Then 35 g of a proteinase ADK-2 (mfd. by Asahi Danka Kogyo, K.K.) dissolved in a small amount of water was added thereto.

The obtained mixture was stirred at a high rate for 30 minutes while maintaining the temperature at 50±2° C. and then heated to 95° C. to thereby inactivate the enzyme. After pasteurizing at 100° C. for 10 minutes, 5-kg portions of the mixture were packaged. Thus a proteinous material containing 40% by weight of solid matters, which was in the form of a pale red and viscous paste, was obtained.

This proteinous material contained 32% by weight of water-soluble proteins, based on the total proteins, as determined by the precipitation method in a solution of trichloroacetic acid and 1.0% by weight of chitin.

By spray-drying the proteinous material, a crab powder having a characteristic flavor was obtained.

What is claimed is:

1. A process for preparing a pasty proteinous material or a proteinous food from crustacean materials comprising residual meat, bones and carapaces which comprises:
   inactivating enzymes contained in said crustaceans by heating to sufficient temperature(s) for inactivating the enzymes and milling said crustaceans materials to such an extent as to reduce the particle size of said crustacean materials to 200 microns or less; and thereafter
   reacting said crustacean materials with proteolytic enzyme(s) or proteolytic microorganism(s) for both until there is produced a 5 to 50% content of water-soluble proteins, based on the total proteins, in the pasty proteinous material or proteinous food and a 40 to 90% content of peptides of molecular weight of 40,000 to 70,000, based on the total peptides except water-soluble peptides and amino acids, in the pasty proteinous material or proteinous food.

2. The process for preparing a pasty proteinous material or a proteinous food from crustaceans as set forth in claim 1, wherein said particle size of the crustacean materials is 150 microns or below.

3. The process for preparing a pasty proteinous material or a proteinous food from crustacean material as set forth in claim 1, wherein said content of water-soluble proteins, based on the total proteins, in the pasty proteinous material or a proteinous food is 30 to 45%.

4. The process for preparing a pasty proteinous material or proteinous food from crustacean materials as set forth in claim 1 wherein the milling of the crustacean materials is carried out before the inactivating of the enzymes.

5. The process for preparing a pasty proteinous material or proteinous food from crustacean materials as set forth in claim 1 wherein the milling of the crustacean materials is carried out at the same time as the inactivating of the enzymes.

6. A process for preparing a pasty proteinous material or a proteinous food from crustacean materials comprising residual meat, bones and carapaces which comprises:
   inactivating enzyme contained in said crustacean materials by adding thereto, sufficient hydrogen peroxide for inactivating the enzymes, thereafter heating to a temperature that is lower than the temperature required for the inactivating enzymes and is lower than the temperature for gelatin of the proteins contained in said crustacean materials, and milling said crustacean materials to such an extent as to reduce the particle size of said crustacean materials to 200 microns or below; and
   thereafter reacting said crustacean materials with a proteolytic enzyme or proteolytic micoorganism or both until there is produced a 5 to 50% content of water-soluble proteins, based on the total proteins, in the pasty proteinous material or proteinous food, and a 40 to 90% content of peptides of molecular weight of 40,000 to 70,000 based on the total peptides except water-soluble peptides and amino acids, in the pasty proteinous material or proteinous food.

7. The process for preparing a pasty proteinous material or a proteinous food from crustacean materials as set forth in claim 6, wherein said particle size of the crustacean materials is 150 microns or less.

8. The process for preparing a pasty proteinous material or a proteinous food from crustacean materials, as set forth in claim 6, wherein said content of water-soluble proteins, based on the total proteins, in the pasty proteinous material or a proteinous food is 30 to 45%.

9. The process for preparing a pasty proteinous material or proteinous food from crustacean materials as set forth in claim 6 wherein the milling of the crustacean materials is carried out before the inactivating of the enzymes.

10. The process for preparing a pasty proteinous material or proteinous food from crustacean materials as set forth in claim 6 wherein the milling of the crustacean materials is carried out at the same time as the inactivating of the enzymes.

* * * * *